US011678891B2

(12) United States Patent
Okamura

(10) Patent No.: US 11,678,891 B2
(45) Date of Patent: Jun. 20, 2023

(54) HEMOSTATIC DEVICE AND HEMOSTATIC METHOD

(71) Applicant: TERUMO KABUSHIKI KAISHA, Tokyo (JP)

(72) Inventor: Ryo Okamura, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 583 days.

(21) Appl. No.: 16/601,858

(22) Filed: Oct. 15, 2019

(65) Prior Publication Data

US 2020/0038038 A1    Feb. 6, 2020

Related U.S. Application Data

(63) Continuation of application No. 16/148,501, filed on Oct. 1, 2018, now Pat. No. 10,492,797, which is a
(Continued)

(30) Foreign Application Priority Data

Mar. 29, 2017  (JP) .............................. JP2017-066143

(51) Int. Cl.
 *A61B 17/135* (2006.01)
 *A61B 90/00* (2016.01)
(Continued)

(52) U.S. Cl.
 CPC ........ *A61B 17/135* (2013.01); *A61B 17/1325* (2013.01); *A61B 90/08* (2016.02);
(Continued)

(58) Field of Classification Search
 CPC .............. A61B 17/132; A61B 17/1322; A61B 17/1325; A61B 17/1327; A61B 17/135;
(Continued)

(56) References Cited

U.S. PATENT DOCUMENTS 4,393,867 A    7/1983  Baron
4,470,410 A *  9/1984  Elliott .................... A61M 25/02
                                          128/877
(Continued)

FOREIGN PATENT DOCUMENTS

CN    102834139 A    12/2012
JP      59035621 B2   8/1984
(Continued)

OTHER PUBLICATIONS

Office Action (Notice of Reasons for Refusal) dated Sep. 15, 2020, by the Japanese Patent Office in corresponding Japanese Patent Application No. 2019-223623 and an English Translation of the Office Action. (6 pages).
(Continued)

*Primary Examiner* — Ashley L Fishback
*Assistant Examiner* — Christian D Knauss
(74) *Attorney, Agent, or Firm* — Buchanan Ingersoll & Rooney PC

(57) ABSTRACT

A hemostatic device can perform hemostasis by compressing a puncture site on a hand of a patient, and can prevent a movable range of fingers from being narrowed or can prevent misalignment at a wearing position, when the hemostatic device is worn on the hand. The hemostatic device has a covering portion to cover a site where bleeding is to be stopped on a hand of a patient, and a pressing portion that compresses the site where bleeding is to be stopped, in a state where the covering portion covers the site where bleeding is to be stopped. The covering portion includes a securing portion that surrounds at least a portion of the hand while covering the pressing portion, and a restriction portion that restricts a movement of the securing portion in an axial direction. The restriction portion is disposed between adjacent fingers and of the hand.

19 Claims, 17 Drawing Sheets

Related U.S. Application Data continuation of application No. PCT/JP2018/012436, filed on Mar. 27, 2018.

(51) Int. Cl.
*A61B 17/132* (2006.01)
*A61B 17/00* (2006.01)
*A61B 17/12* (2006.01)

(52) U.S. Cl.
CPC .... *A61B 90/39* (2016.02); *A61B 2017/00907* (2013.01); *A61B 2017/12004* (2013.01); *A61B 2090/0811* (2016.02); *A61B 2090/3937* (2016.02)

(58) Field of Classification Search
CPC ...... A61B 17/1355; A61B 2017/12004; A61H 39/04; A61F 5/01; A61F 5/012; A61F 5/013; A61F 5/05866; A61F 5/30; A61F 5/32; A61F 5/34; A61F 2007/0035; A61F 2007/0036; A61F 13/04
See application file for complete search history.

(56) References Cited

U.S. PATENT DOCUMENTS

| | | | |
|---|---|---|---|
| 5,404,591 | A | 4/1995 | Brinnand et al. |
| 6,146,347 | A | 11/2000 | Porrata |
| 8,277,419 | B1 | 10/2012 | Spitaleri |
| 2004/0098035 | A1* | 5/2004 | Wada ............... A61B 17/135 606/201 |
| 2005/0187566 | A1 | 8/2005 | Byrum |
| 2006/0190026 | A1 | 8/2006 | Sanders |
| 2011/0040258 | A1 | 2/2011 | Robison |
| 2012/0116444 | A1* | 5/2012 | Zodnik ............... A61B 17/135 606/202 |
| 2012/0296369 | A1 | 11/2012 | Atthoff et al. |
| 2013/0023734 | A1 | 1/2013 | Okamura |
| 2015/0018868 | A1* | 1/2015 | Pancholy ............... A61B 17/12 606/202 |
| 2015/0342615 | A1 | 12/2015 | Keinan et al. |
| 2018/0042615 | A1 | 2/2018 | Kimura et al. |
| 2019/0029693 | A1 | 1/2019 | Okamura |

FOREIGN PATENT DOCUMENTS

| | | |
|---|---|---|
| JP | 2008119517 A | 5/2008 |
| JP | 6655752 B1 | 2/2020 |
| RU | 2005 104 538 A | 7/2006 |
| WO | 2014/205349 A1 | 12/2014 |
| WO | 2016/163326 A1 | 10/2016 |

OTHER PUBLICATIONS

An English Translation of the International Search Report (Form PCT/ISA/210) and the Written Opinion of the International Searching Authority (Form PCT/ISA/237) dated Jun. 19, 2018 by the Japanese Patent Office in corresponding International Application No. PCT/JP2018/012436 (5 pages).

The extended European Search Report dated Dec. 9, 2020, by the European Patent Office in corresponding European Patent Application No. 18774327.3-1122. (8 pages).

Office Action dated Apr. 23, 2020, by the Russian Patent Office in corresponding Russian Patent Application No. 2019130321/14(059640) and an English Translation of the Office Action. (16 pages).

Office Action (The First Office Action) dated Apr. 21, 2022, by the National Intellectual Property Administration in corresponding Chinese Patent Application No. 201880021246.3 and an English Translation of the Office Action. (23 pages).

\* cited by examiner

HEMOSTATIC DEVICE AND HEMOSTATIC METHOD

CROSS-REFERENCES TO RELATED APPLICATIONS

This application is a continuation of U.S. application Ser. No. 16/148,501 filed Oct. 1, 2018, which is a continuation of International Application No. PCT/JP2018/012436 filed on Mar. 27, 2018, which claims priority to Japanese Application No. 2017-066143 filed on Mar. 29, 2017, the entire content of all three of which is incorporated herein by reference.

TECHNICAL FIELD

The present invention generally relates to a hemostatic device and a hemostatic method which are used for performing hemostasis by compressing a puncture site of a hand of a patient.

BACKGROUND DISCUSSION

A medical procedure is known in which a medical elongated body (for example, a sheath tube of an introducer) is introduced into a blood vessel via a puncture site formed in the blood vessel of an arm of a patient so as to perform treatment or therapy on a lesion area. In a case where this medical procedure is performed, an operator performs hemostasis on the puncture site when the operator removes the medical elongated body from the puncture site.

As a hemostatic device used for hemostasis of the puncture site, a hemostatic device is known which includes a band for being wrapped around a limb of an arm, and securing means for securing the band in a state of being wrapped around the limb, and an inflatable portion for being inflated by injecting a fluid into the inflatable portion so as to compress the puncture site. An example of this hemostatic device is disclosed in Japanese Application Publication No 2008-119517.

A radial artery or an ulnar artery extending along the arm of a human body is connected to a palmar artery which bypasses a hand side. Therefore, for example, the operator forms the puncture site in the palmar artery, thereby enabling the operator to insert the medical elongated body into the radial artery extending along the arm side. In addition, if the puncture site is formed in the hand rather than the arm or a wrist, a patient can move his or her arm or wrist while the hemostasis is performed (while a compressing force is applied to the puncture site). Accordingly, the patient can more freely move his or her body, and thus, can enjoy improved quality of life (QOL).

Even when the puncture site for introducing the medical elongated body is formed in the hand rather than the arm or the wrist as described above, when the medical elongated body is removed from the puncture site, the operator needs to perform the hemostasis.

SUMMARY

However, when the hemostatic device disclosed in Japanese Application Publication No 2008-119517 is used to perform hemostasis on the puncture site formed on the hand, problems arise in the following points.

The hemostatic device disclosed in Japanese Application Publication No 2008-119517 is not designed in view of a structure of the hand (structure of fingers extending and divided from a dorsal side of the hand or a palm). Therefore, if the hemostatic device is worn on the hand, finger motions of the patient are limited, thereby causing a possibility that the QOL may become poor.

In addition, when the hemostatic device disclosed in Japanese Application Publication No 2008-119517 is used, the operator can secure the hemostatic device to the hand by wrapping the band along the dorsal side of the hand or the palm. However, in terms of whole hand motions allowed by the movable fingers when the hemostatic device is worn on the hand, the hemostatic device cannot obtain a sufficient securing force only by securing the band. Consequently, there is a possibility that misalignment may be likely to occur when the hemostatic device is worn on the hand.

The hemostatic device disclosed here can perform hemostasis by compressing a puncture site on a hand of a patient, and which can prevent a movable range of fingers from being narrowed or can prevent misalignment when the hemostatic device is worn on the hand, and a hemostatic method which enables the hemostasis to be preferably performed on the puncture site on the hand of the patient.

According to one aspect, a hemostatic device includes a covering portion configured to cover a site where bleeding is to be stopped on a hand of a patient, a pressing portion that compresses the site where bleeding is to be stopped when the covering portion covers the site where bleeding is to be stopped, and a marker portion for aligning the pressing portion with the site where bleeding is to be stopped so that the pressing portion overlies the site where bleeding is to be stopped. The covering portion includes a securing portion configured to surround at least a portion of the patient's hand while covering the pressing portion, and a restriction portion that restricts movement of the securing portion in an axial direction and that is positionable between adjacent fingers of the patient's hand. The securing portion includes a band portion wrappable around a periphery of the patient's hand at the site where bleeding is to stopped, with the band portion including a midpoint between oppositely located first and second free ends of the band portion. The pressing portion is mounted on the band portion at an intermediate position between the first and second free ends of the band portion, with the pressing portion being located closer to the first free end of the band portion than the second free end of the band portion. The band portion includes an elongated part that extends from the second free end of the band portion toward the pressing portion, with the elongated part of the band portion possessing a centerline that extends along the elongated part of the band portion from the second free end to the midpoint of the band portion. A holding portion secures the band portion in a state in which the band portion is wrapped around the periphery of the patient's hand at the site where bleeding is to stopped. The restriction portion includes a first end portion secured to the band portion, a second end portion that is a free end portion configured to be freely detachably interlocked with the band portion, and a midpoint between the first end portion of the restriction portion and the second free end portion of the restriction portion. An elongated part extends from the second free end portion of the restriction portion toward the band portion, with the elongated part of the restriction portion possessing a centerline that extends along the elongated part of the restriction portion from the second free end portion to the midpoint of the restriction portion. The centerline of the elongated part of the restriction portion and the centerline of the elongated part of the band portion forming an included angle that is an obtuse angle.

According to another aspect, a method of performing hemostasis on a puncture site of a hand of a patient involves positioning a hemostatic device relative to the puncture site where bleeding is to be stopped so that a covering portion of the hemostatic device covers the puncture site on the hand of the patient where bleeding is to be stopped. The covering portion includes a securing portion and a restriction portion, with the securing portion being comprised of a band portion possessing opposite ends and holding portion, and the restriction portion possessing one end fixed relative to the band portion and projecting away from the band portion toward a free end of the restriction portion. The positioning of the hemostatic device relative to the puncture site where bleeding is to be stopped comprises positioning the pressing portion to overlie the puncture site on the hand of the patient where bleeding is to be stopped, and the positioning of the pressing portion to overlie the puncture site on the hand of the patient where bleeding is to be stopped comprising positioning the pressing portion to overlie the puncture site on the hand of the patient where bleeding is to be stopped while a medical elongated body indwells the puncture site. The method further includes securing the covering portion to the patient's hand by: i) wrapping the band portion of the securing portion around at least a portion of a periphery of the patient's hand while the band portion covers the pressing portion; ii) securing the band portion in a state in which the band portion is wrapped around at least the portion of the periphery of the patient's hand by releasably engaging the holding portions of the band portion with one another; iii) positioning a part of the restriction portion between a thumb and forefinger on the patient's hand; and iv) releasably fastening a portion of the restricting portion to the band portion to restrict movement of the expandable pressing portion in an axial direction The method also involves applying a compressing force to the puncture site of the patient's hand by way of the pressing portion, and removing the medical elongated body from the puncture site while maintaining the compressing force applied to the puncture site of the patient's hand by the pressing portion.

According to a further aspect, a method of performing hemostasis on a puncture site of a hand of a patient comprises positioning a hemostatic device relative to the puncture site where bleeding is to be stopped so that a covering portion of the hemostatic device covers the puncture site on the hand of the patient where bleeding is to be stopped, wherein the covering portion includes a securing portion and a restriction portion. The securing portion is comprised of a band portion possessing opposite ends and a holding portion, the restriction portion possesses one end fixed relative to the band portion and projecting away from the band portion toward a free end of the restriction portion. The hemostatic device also includes a pressing portion and a marker portion for aligning the pressing portion with the puncture site where bleeding is to be stopped. The positioning of the hemostatic device relative to the puncture site where bleeding is to be stopped comprises positioning the pressing portion to overlie the puncture site on the hand of the patient where bleeding is to be stopped, with the positioning of the pressing portion to overlie the puncture site being performed by using the marker to position the pressing member relative to the puncture site where bleeding is to be stopped. The method also includes securing the covering portion to the patient's hand by: i) wrapping the band portion of the securing portion around at least a portion of a periphery of the patient's hand while the band portion covers the pressing portion; ii) securing the band portion in a state in which the band portion is wrapped around at least the portion of the periphery of the patient's hand by releasably engaging the holding portions of the band portion with one another; iii) positioning a part of the restriction portion between a thumb and forefinger on the patient's hand; and iv) releasably fastening a portion of the restricting portion to the band portion to restrict movement of the expandable pressing portion in an axial direction. The method additionally includes applying a compressing force to the puncture site of the patient's hand by way of the pressing portion.

The above-described hemostatic device can perform the hemostasis by causing the pressing portion to compress the puncture site, in a state where the covering portion covers the site where bleeding is to be stopped on the hand of the patient. Then, in a state where the hemostatic device is worn on the hand of the patient, while the hemostatic device is secured by the securing portion surrounding the hand, the movement of the securing portion in the axial direction (extending direction of fingers) is restricted by the restriction portion disposed between the adjacent fingers of the hand. In this manner, according to the hemostatic device, it is possible to prevent a movable range of the fingers from being narrowed, or to prevent misalignment when the hemostatic device is worn on the hand.

According to the above-described hemostatic method, the hemostasis is performed on the puncture site formed on the radial artery side of the palmar artery of the patient, thereby preventing motions of the arm or the wrist of the patient from being limited while the hemostasis is performed. In this manner, the patient can more freely move his or her body. Accordingly, QOL is improved.

BRIEF DESCRIPTION OF THE DRAWINGS

FIG. 3(A) is a perspective view when viewed from a side of a dorsal side of the hand, and FIG. 3(B) is a perspective view when viewed from a palm side.

FIG. 12(A) is a perspective view when viewed from a side of the dorsal side of the hand, and FIG. 12(B) is a perspective view when viewed from the palm side.

FIG. 14(A) is a perspective view when viewed from a side of the dorsal side of the hand, and FIG. 14(B) is a perspective view when viewed from the palm side.

FIG. 17(A) is a perspective view when viewed from a side of the dorsal side of the hand, and FIG. 17(B) is a perspective view when viewed from the palm side.

DETAILED DESCRIPTION

Figure 1:
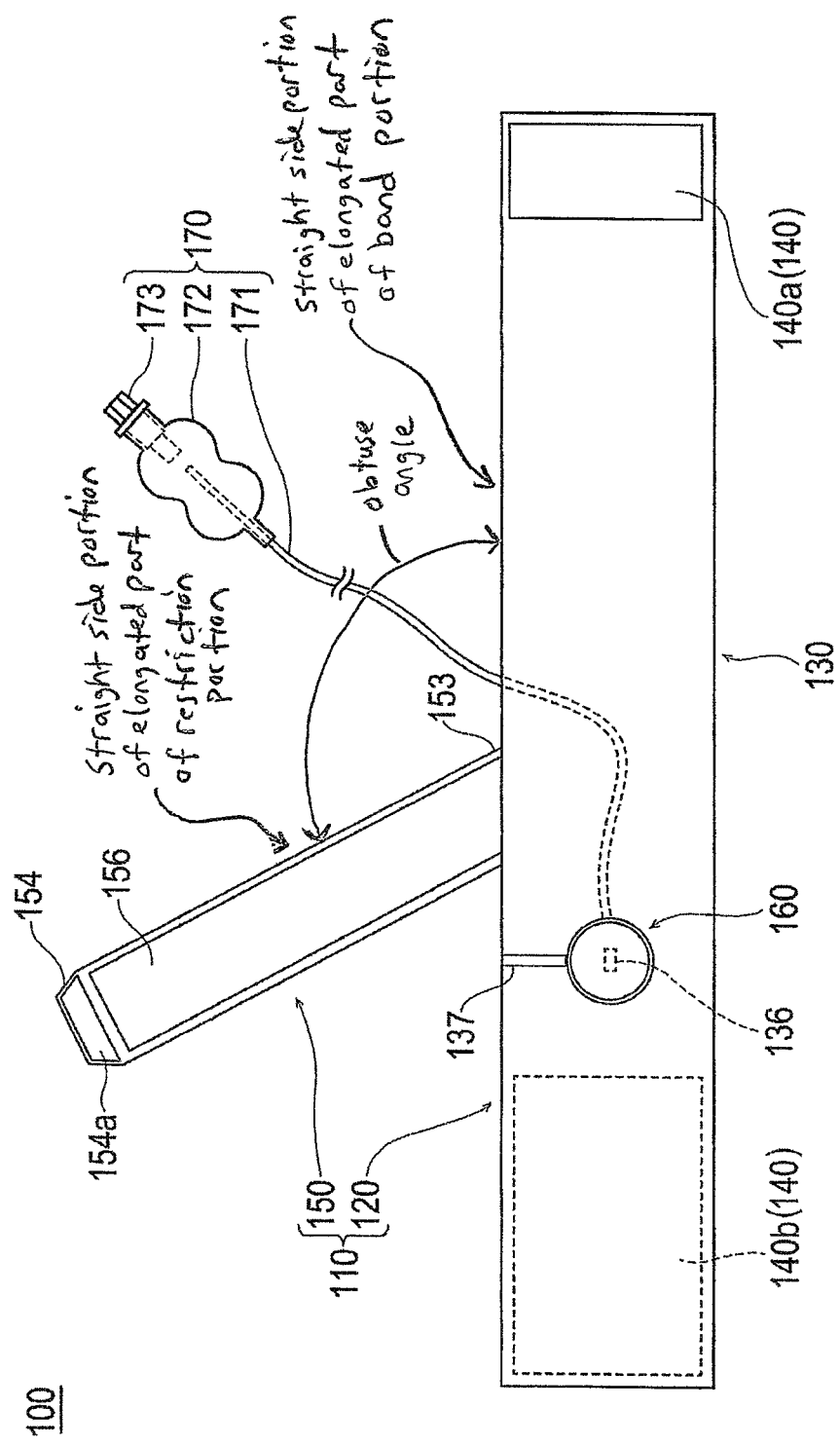
FIG. 1 is a plan view when a hemostatic device according to a first embodiment is viewed from an inner surface side.

Set forth below with reference to the accompanying drawings is a detailed description of embodiments of a hemostatic device and a hemostatic method representing examples of the inventive hemostatic device and a hemostatic method disclosed here. The dimensions or scales on the drawings may be exaggerated or different from actuality/reality for convenience of description and illustration. The following description does not limit the technical scope or the meaning of terms described in the appended claims.

First Embodiment

A hemostatic device 100 according to a first embodiment will be described with reference to FIGS. 1 to 10. FIGS. 1 to 5 are views for describing a configuration of the hemostatic device 100. FIG. 6 is a view for describing each blood vessel extending along a hand H of a patient. FIGS. 7 to 10 are views for describing a wearing procedure of the hemostatic device 100 and a procedure in a hemostatic method of using the hemostatic device 100.

The hemostatic device 100 according to the present embodiment is used as follows. As illustrated in FIGS. 7 to 10, the hemostatic device 100 is used to perform hemostasis on a puncture site t2 after removing a sheath tube 210 (corresponding to a "medical elongated body") of an introducer 200 indwelling the puncture site t2 formed on a radial artery side Pdr of a palmar artery Pa (deep palmar artery Pd) of the hand H of the patient.

Prior to the description of the hemostatic device 100, the hand H of the patient who is a wearing target of the hemostatic device 100 and blood vessels extending along or running on the hand H will be described with reference to FIG. 6. FIG. 6 schematically illustrates the hand (right hand) H of the patient, in plan view, when the hand H of the patient is viewed from a side of a the dorsal side Hb of the hand.

A radial artery Ra and an ulnar artery Ua which are divided or split from a brachial artery in the vicinity of an elbow run on or extend along an arm A of the patient. The radial artery Ra and the ulnar artery Ua are connected to each other in an arch shape (bow shape) on the hand H, thereby forming the palmar artery (palmar artery arch) Pa. In addition, the palmar artery Pa includes a deep palmar artery (deep palmar artery arch) Pd formed from a deep palmar branch where the radial artery Ra and the ulnar artery Ua are divided on the side of the dorsal side Hb of the hand, and a superficial palmar artery (superficial palmar artery arch) Pf formed from a superficial palmar branch where the radial artery Ra and the ulnar artery Ua are divided on the palm Hp side.

According to the present embodiment, when a virtual line C which divides the palmar artery Pa at a substantially center position in a width direction (rightward-leftward direction in FIG. 6) of the hand H is set as a boundary, a portion (region) extending to the radial artery Ra side in the deep palmar artery Pd included in the palmar artery Pa is defined as a radial artery side Pdr (hereinafter, also referred to as the "radial artery side Pdr of the palmar artery Pa") of the deep palmar artery Pd. A portion (region) extending to the ulnar artery Ua side in the deep palmar artery Pd included in the palmar artery Pa is defined as an ulnar artery side Pdu of the deep palmar artery Pd.

In addition, when the virtual line C illustrated in FIG. 6 is set as the boundary, a portion (region) extending to the radial artery Ra side in the superficial palmar artery Pf included in the palmar artery Pa is defined as a radial artery side Pfr of the superficial palmar artery Pf. A portion (region) extending to the ulnar artery Ua side in the superficial palmar artery Pf included in the palmar artery Pa is defined as an ulnar artery side Pfu of the superficial palmar artery Pf.

An inter-finger portion (inter-finger web) Fb is present between respectively adjacent fingers F1 to F5 (a thumb F1, a forefinger F2, a middle finger F3, a ring finger F4, and a little finger F5). A fingertip direction of the respective fingers F1 to F5 is indicated by an arrow A1, and a direction from the wrist W and the arm A toward an elbow side is indicated by an arrow A2. In the description herein, the direction indicated by the arrows A1-A2 is set as an "axial direction".

According to the present embodiment, the hand H is defined as a portion including the dorsal side Hb of the hand and the palm Hp which are located on the fingertip side from the wrist (joint connecting the palm and the arm to each other) W. In FIG. 6, a boundary portion between the wrist W and the hand H is illustrated using a virtual line B.

Figure 4:
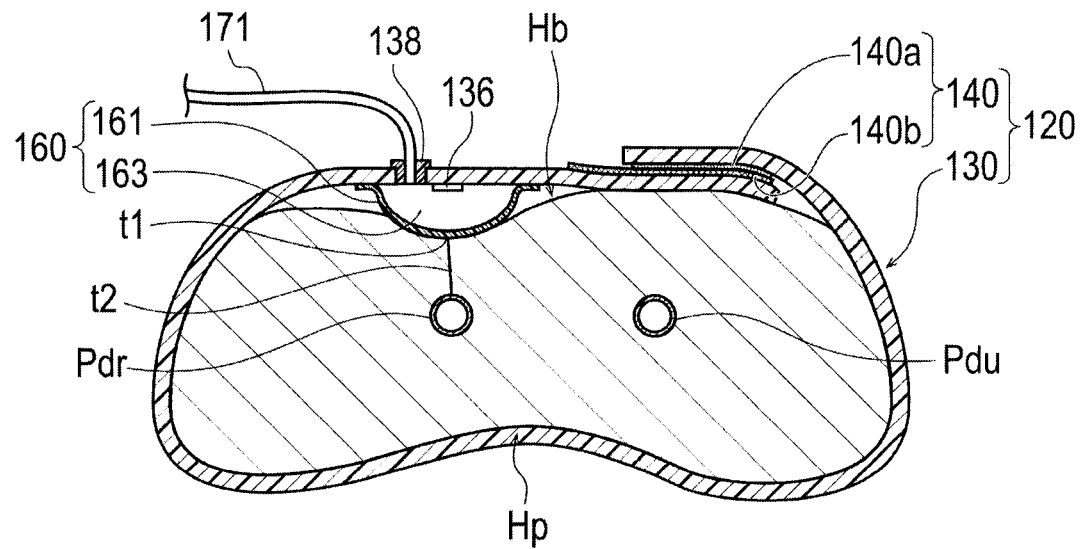
FIG. 4 is a cross-sectional view (cross-sectional view of the hand) taken along the section line 4-4 illustrated in FIG. 3(A).

As illustrated in FIG. 4, according to the present embodiment, the "site where bleeding is to be stopped t1" means a perforation formed in a skin surface layer of the patient by a medical instrument such as a puncture needle and a peripheral portion of the puncture needle. The "puncture site t2" means a subcutaneous portion (including the blood vessel) of a living body in which the perforation is formed by the medical instrument such as the puncture needle.

In addition, according to the present embodiment, the puncture site t2 is formed on the radial artery side Pdr of the palmar artery Pa (refer to FIGS. 4 and 6). More specifically, as illustrated in FIG. 6, for example, in a state where the hand H of the patient is open, the puncture site t2 is formed between a center line c1 of the thumb F1 on the side of the dorsal side Hb of the hand and a center line c2 of the forefinger F2 (a position where the center line c1 and the center line c2 intersect each other or a peripheral portion thereof).

Next, the hemostatic device 100 will be described.

Figure 2:
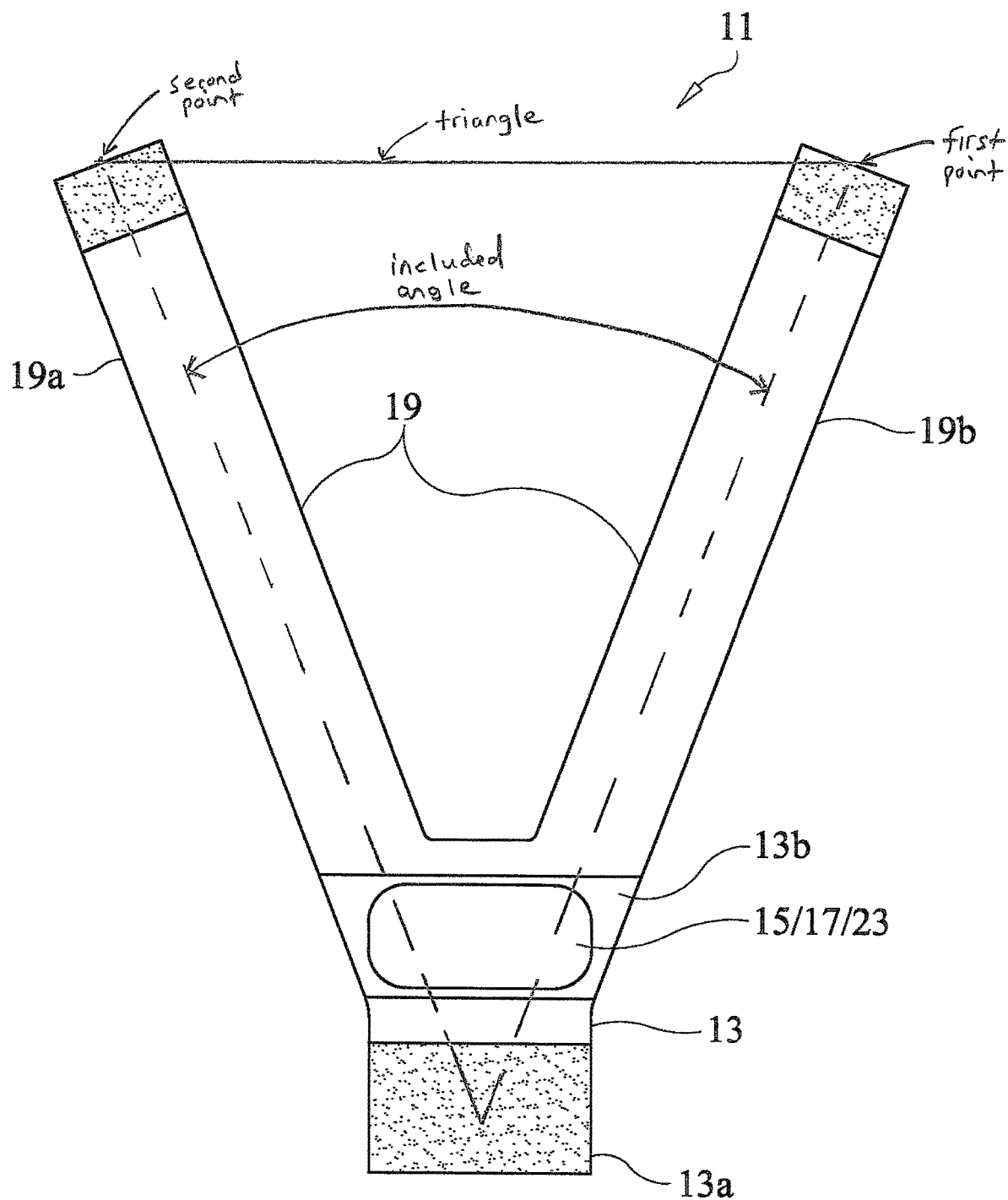
FIG. 2 is a plan view illustrating a state where the hemostatic device according to the first embodiment is worn on a hand of a patient.
Figure 3A:
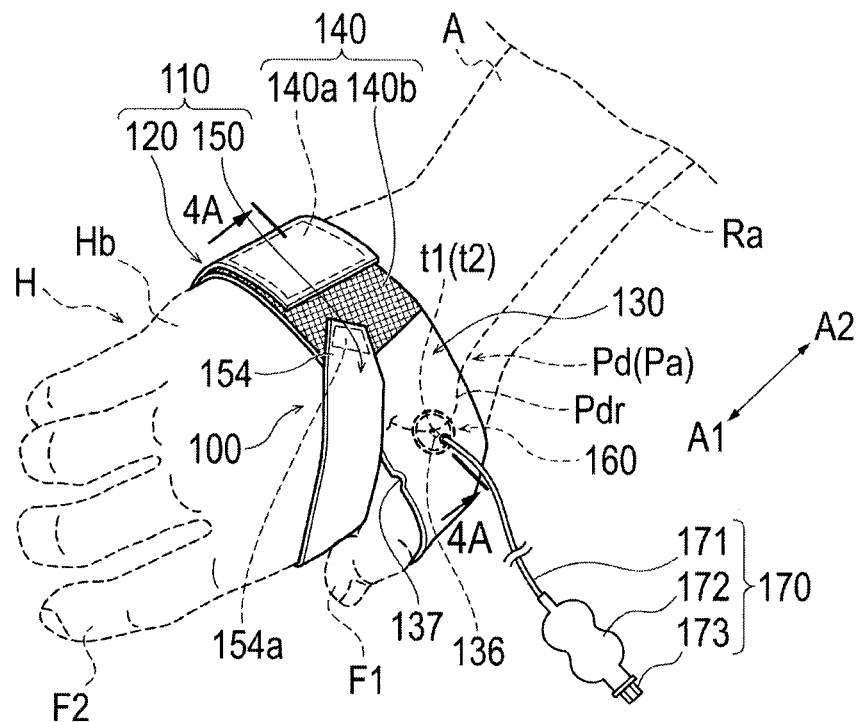
FIGS. 3(A) and 3(B) are perspective views illustrating a state where the hemostatic device according to the first embodiment is worn on the hand of the patient.
Figure 3B:
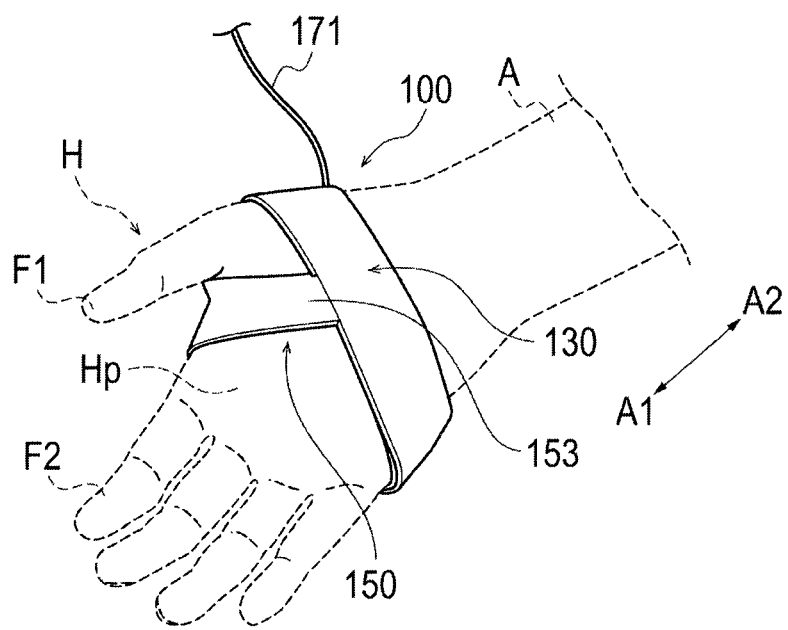

As illustrated in FIGS. 1 to 3, the hemostatic device 100 includes a covering portion 110 disposed so as to cover the site where bleeding is to be stopped t1 on the hand H of the patient, and a pressing portion 160 that compresses or applies a compressive force to the site where bleeding is to be stopped t1 in a state where the covering portion 110 covers the site where bleeding is to be stopped t1.

As illustrated in FIGS. 1 and 2, the covering portion 110 has a securing portion 120 which surrounds at least a portion of the hand H while covering the pressing portion 160, and a restriction portion 150 which restricts movement of the securing portion 120 in the axial direction.

As illustrated in FIGS. 1 and 3, the securing portion 120 includes a band portion (band) 130 wrapped around the site where bleeding is to be stopped t1 on the hand H, and a holding portion 140 which secures the band portion 130 in a state where the band portion 130 is wrapped around a periphery of the hand H.

As illustrated in FIG. 1, the band portion 130 is configured to include a flexible band-like or band-shaped member. In the description herein, when the band portion 130 is wrapped around the hand H, a surface (wearing surface) on a side facing a body surface of the hand H will be referred to as an "inner surface", and a surface on a side opposite the inner surface will be referred to as an "outer surface". FIG. 1 illustrates a plan view of the hemostatic device 100 when viewed from the inner surface side of the band portion 130.

As illustrated in FIGS. 3 and 4, the band portion 130 is wrapped substantially once round around an outer periphery of the hand H.

In the band or band portion 130, a male side (or a female side) 140a of a surface fastener generally called a Magic Tape (registered trademark) is disposed on the inner surface side of a portion in the vicinity of the right end in FIG. 1. In addition, in the band portion 130, a female side (or a male side) 140b of the surface fastener is disposed on the outer surface side of a portion in the vicinity of the left end in FIG. 1.

The male side 140a of the surface fastener of the band portion 130 and the female side 140b of the surface fastener of the band portion 130 configure or constitute the holding portion 140. As illustrated in FIGS. 2 and 4, the operator wraps the band portion 130 around the hand H, and joins the male side 140a of the surface fastener and the female side 140b of the surface fastener to each other. In this manner, the operator can secure the band portion 130 to the hand H of the patient.

The holding portion 140 is not particularly limited as long as the holding portion 140 has a configuration capable of securing the band portion 130 in a state where the band portion 130 is wrapped around the hand H. For example, the configuration may be a snap, a button, a clip, or a frame member passing through the end portion of the band portion 130, for example.

As shown in FIG. 1, the covering portion 110 is comprised of a first band part (to the right of the pressing portion 160 in FIG. 1) that extends away from the pressing portion 160 in one direction and that has one end fixed relative to the pressing portion 160 and an opposite free end at which the fastener 140a is located, and a second band part (to the left of the pressing portion 160 in FIG. 1) that extends away from the pressing portion 160 in another direction and that has one end fixed relative to the pressing portion 160 and an opposite free end at which is located a fastener 140b. The covering portion 110 also includes a third band part 150 that includes one end 153 fixed relative to the pressing portion 160 and an opposite free end 154 at which is located a fastener 154a.

A material forming the band portion 130 is not particularly limited, as long as the material is flexible. For example, this material includes polyolefin such as polyvinyl chloride, polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, or any optional combination thereof (blend resin, polymer alloy, and laminate).

In addition, it is preferable that a portion of the band portion 130 overlapping at least the pressing portion 160 in the band portion 130 is substantially transparent. However, without being limited to transparency, the above-described portion of the band portion 130 may be translucent or colored transparent. Since the band portion 130 is formed in this way, when the hemostatic device 100 is worn on the hand H of the patient (refer to FIG. 8), the operator can visually confirm the site where bleeding is to be stopped t1 from the outer surface side of the band portion 130. Therefore, the operator can relatively easily align a marker portion or marker 136 (to be described later) with the site where bleeding is to be stopped t1.

Figure 5:
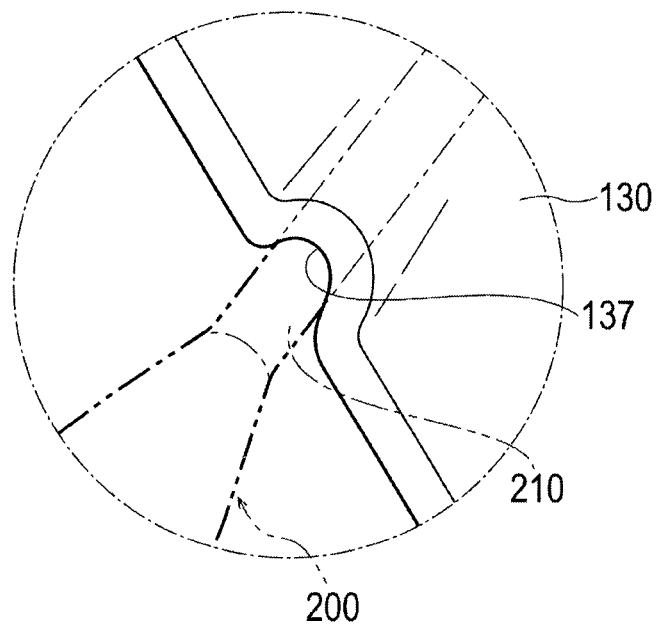
FIG. 5 is an enlarged perspective view of an indwelling portion of the hemostatic device according to the first embodiment.
Figure 6:
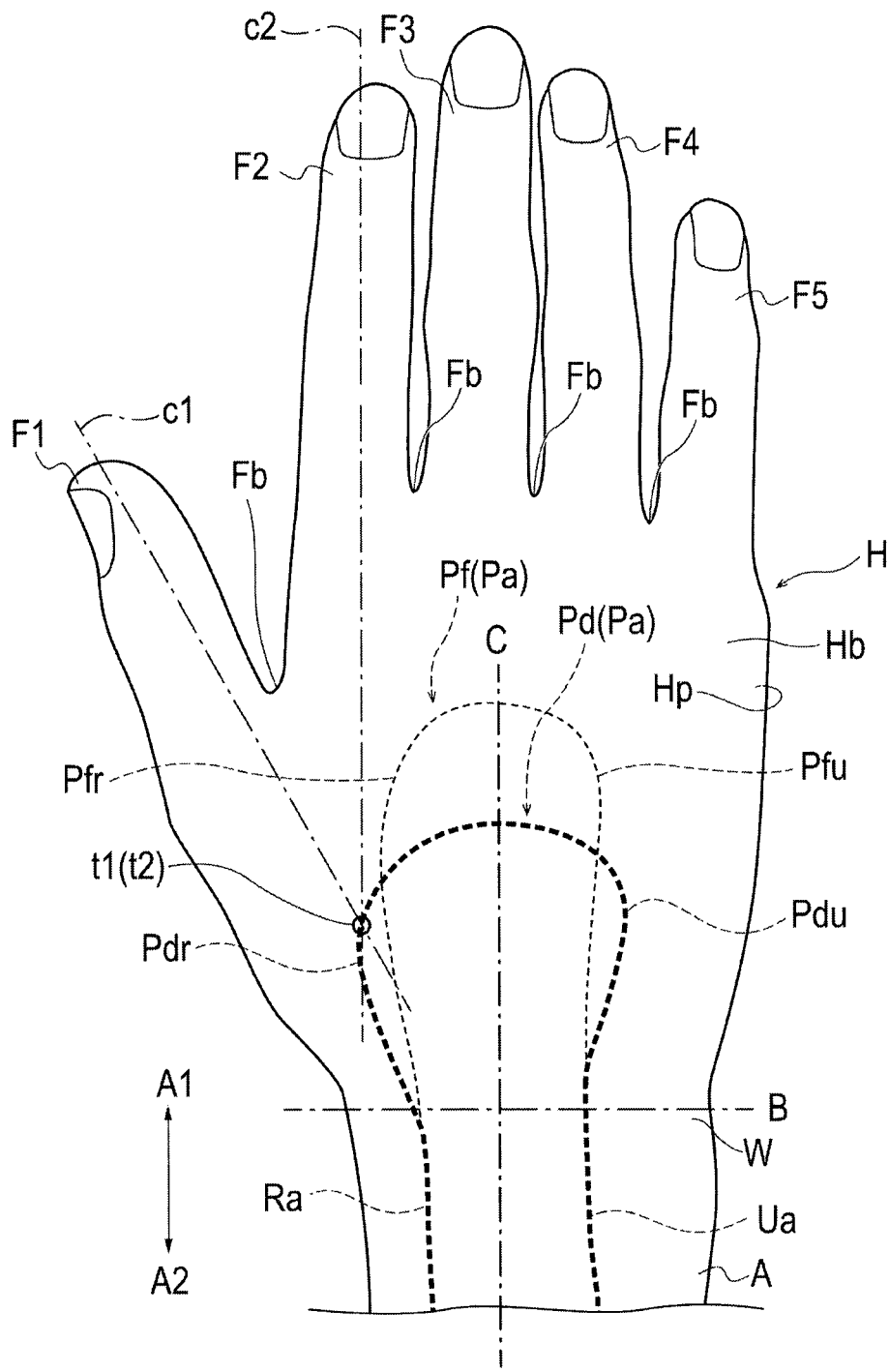
FIG. 6 is a plan view schematically illustrating a structure of the hand of the patient.

As illustrated in FIGS. 1 and 5, the covering portion 110 has an indwelling portion 137 enabling the sheath tube 210 of the introducer 200 to indwell the site where bleeding is to be stopped t1.

As illustrated in FIG. 1, the indwelling portion 137 is formed on an inner surface of the band portion 130. As illustrated in FIG. 5, the indwelling portion 137 is formed from a groove in which the sheath tube 210 of the introducer 200 can be disposed. The groove configuring the indwelling portion 137 has a curved shape which is concave in a thickness direction of the band portion 130 from the inner surface side of the band portion 130. As illustrated in FIG. 1, in the indwelling portion 137, one end side is formed so as to face the outer surface of the band portion 130, and the other end side extends to the vicinity of the pressing portion 160.

The specific shape or structure of the indwelling portion 137 is not limited to the grooves as illustrated. For example, the indwelling portion 137 may be a hole portion (opening portion) formed in the vicinity of the pressing portion 160 of the band portion 130.

As illustrated in FIGS. 2 and 3, in a state where the band portion 130 is wrapped around the hand H, the restriction portion 150 is secured to the band portion 130 after passing through an inter-finger portion Fb between the thumb F1 and the forefinger F2.

The restriction portion 150 is configured to include a flexible band-like member. As a material of the restriction portion 150, for example, it is possible to use a material the same as that of the band portion 130. Similar to the band portion 130, the restriction portion 150 may be formed to be transparent (including translucent and colored transparent), or may be a predetermined color so that the restriction portion 150 is not transparent.

As illustrated in FIGS. 1 and 3, the restriction portion 150 has a first end portion 153 secured to the band portion 130 and a second end portion 154 opposing the first end portion 153 at the opposite end of the restriction portion 150 and capable of freely detachably interlocking with the band portion 130.

As illustrated in FIG. 1, in a state where the second end portion 154 is separated from the band portion 130, the restriction portion 150 extends while being inclined at a predetermined angle in an extending direction (rightward-leftward direction in FIG. 1) of the band portion 130. By way of example, The restriction portion 150 may be formed to have a width smaller than a width of the band portion 130. The width of the band portion 130 is a dimension in a direction orthogonal to the extending direction of the band portion 130. The width of the restriction portion 150 is a dimension orthogonal to the extending direction of the restriction portion 150. The width of the restriction portion 150 may be the same as the width of the band portion 130.

By way of example, the restriction portion 150 can be formed so that a length in the extending direction is 10 mm to 300 mm and the width is 3 mm to 60 mm. In addition, as another example, the band portion 130 can be formed so that the length in the extending direction is 30 mm to 500 mm and the width is 3 mm to 100 mm. It is preferable that the band portion 130 has a width wider than the width of the restriction portion 150. In this manner, in a state where the hemostatic device 100 is worn on the hand H of the patient, while the pressing portion 160 is more reliably secured to the where bleeding is to be stopped t1 on the hand H of the patient by the band portion 130, the movement in the axial direction (extending direction of the fingers) can be restricted by the restriction portion 150 disposed between the adjacent fingers of the hand.

The second end portion 154 of the restriction portion 150 has a male side (or a female side) 154*a* of the surface fastener. As illustrated in FIG. 2, the operator can interlock the restriction portion 150 with the band portion 130 by joining the male side 154*a* of the surface fastener of the restriction portion 150 and the female side 140*b* of the surface fastener of the band portion 130.

As an example, the restriction portion 150 may be configured to be disposed between fingers other than the thumb F1 and the forefinger F2. In addition, for example, a plurality of the restriction portions 150 can be disposed in one hemostatic device 100. In this case, the restriction portion 150 may be configured to have a plurality of portions which are divided from the restriction portion 150 and are disposed between different fingers, and may be configured to have a plurality of portions which are divided from the band portion 130 and are disposed between different fingers. In addition, for example, the restriction portion 150 may be formed integrally with the band portion 130 such that the restriction portion 150 cannot be attached to or detached from the band portion 130. In a case where the restriction portion 150 has the plurality of portions disposed between the respective fingers, for example, some may be attachable to and detachable from the band portion 130, and some may not be attachable to and detachable from the band portion 130.

Figure 8:
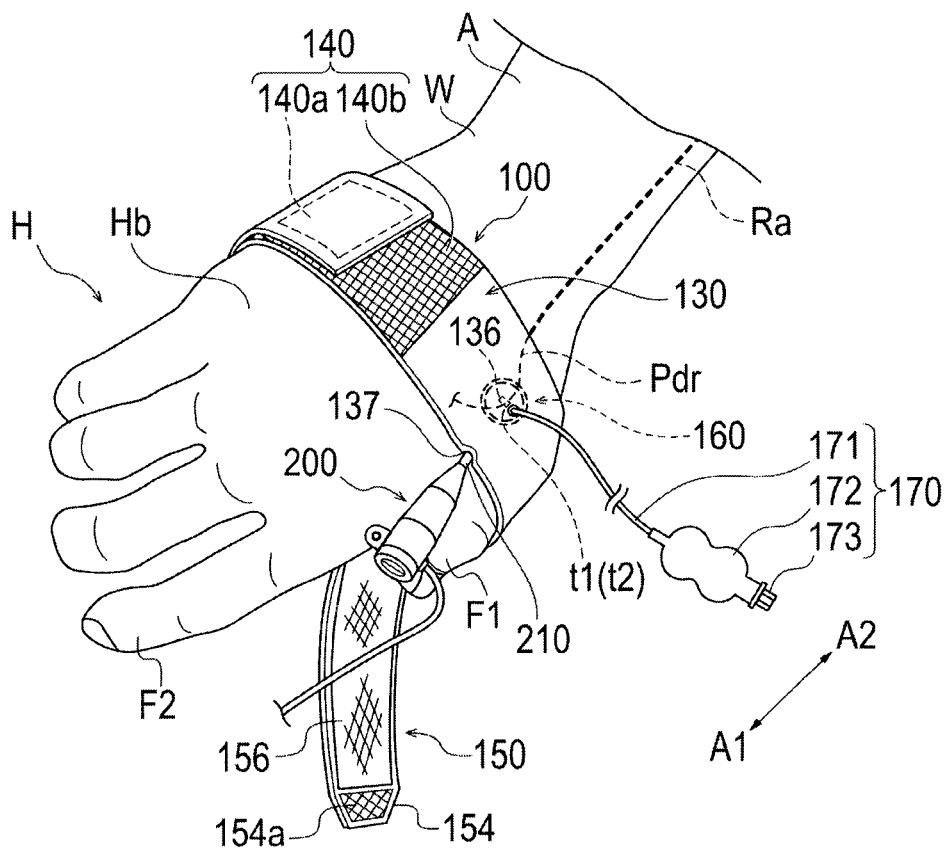
FIG. 8 is a perspective view for describing a wearing procedure and a hemostatic method of the hemostatic device according to the first embodiment.

As illustrated in FIGS. 1 and 8, the restriction portion 150 has a liquid absorbing layer 156 having a liquid absorbing property in a portion (inner surface of the restriction portion 150) disposed on a surface layer side of the hand H.

For example, the liquid absorbing layer 156 can be formed of a gel having the liquid absorbing property (water absorbing property), and a fibrous material or a porous material having the liquid absorbing property. The liquid absorbing layer 156 may be formed on at least a portion of the inner surface of the restriction portion 150, and may not be formed in the entire extending direction of the restriction portion 150.

As illustrated in FIG. 4, the pressing portion 160 has an inflatable member 161 and an inflatable space 163 into which a fluid (for example, air) can be injected.

As illustrated in FIG. 4, the pressing portion 160 is inflated by injecting the fluid into the pressing portion 160, and the compressing force is applied to the site where site bleeding is to be stopped t1 (puncture site t2) of the hand H of the patient. In addition, as illustrated in FIG. 2, in a state where the second end portion 154 of the restriction portion 150 interlocks with the band portion 130, the pressing portion 160 is disposed on a root side (side indicated by an arrow b1 in FIG. 2, which is in a direction from the virtual line C dividing the palmar artery Pa at a substantially central position in the width direction of the hand H toward the center line c2 of the forefinger F2) of the thumb F1 from the second end portion 154 of the restriction portion 150. FIG. 2 also shows that when the second end portion 154 of the restriction portion 150 is interlocked with the band portion 130, the pressing portion 160 and the marker portion 136 are disposed on a thumb side of the band portion between the first end portion 153 and the second end portion 154.

The inflatable member 161 may be formed from a flexible sheet-like member. A peripheral edge of the inflatable member 161 may be welded (or adhered) to the inner surface of the band portion 130. The inflatable member 161 forms the inflatable space 163 that enables the fluid to be injected between the inflatable member 161 and the inner surface of the band portion 130.

A material forming the inflatable member 161 is not particularly limited, and for example, it is possible to use a material the same as the material of the above-described band portion 130.

It is preferable that the inflatable member 161 is substantially transparent. However, without being limited to transparency, the inflatable member 161 may be translucent or colored transparent.

The pressing portion 160 may be configured to include a bag-like member obtained in such a way that edge portions are adhered or welded by folding one sheet, or may be configured to include a balloon-like member which does not include the edge portion.

In addition, an outer shape of the pressing portion 160 is not particularly limited. For example, in a state where the pressing portion 160 is not inflated, the pressing portion 160 may be provided with the outer shapes such as circular, elliptical, and polygonal shapes in a plan view.

In addition, as long as the compressing force can be applied to the site where bleeding is to be stopped t1, the pressing portion 160 may be configured to include a member which does not have an inflatable function allowed by the fluid injection, for example. That is, the pressing portion need not be an inflatable part that applies the compressive force upon inflation. As an example of this pressing portion 160, for example, it is possible to use a mechanical member in which the amount of pushing (i.e., the magnitude of the compressing force) on the hand H is variable using an external operation such as rotation, a member configured to include a plastic resin material or gel for pushing the hand H so as to provide surface pressure, a member including hydrophilic gel or a wound material (dressing material) brought into contact with the site where bleeding is to be stopped t1, a member including gel which gradually reduces the compressing force by decreasing water content with the lapse of time, an elastic material such as sponge-like substances, aggregates of fibers such as cotton (padding), metal, and a member having a predetermined three-dimensional shape (spherical, ellipsoidal, or triangular pyramid shape), or a member obtained by appropriately combining these materials with each other.

As illustrated in FIGS. 1 and 2, the hemostatic device 100 has an injection portion 170 for inflating and deflating the inflatable member 161 of the pressing portion 160.

As illustrated in FIGS. 1 and 4, the injection portion 170 has a flexible tube 171 in which one end portion of the tube is connected to the pressing portion 160, and a lumen in the tube 171 communicates with the inflatable space 163 of the pressing portion 160, a bag body 172 disposed in a distal portion of the tube 171 so as to communicate with the lumen of the tube 171, and a tubular connector 173 having an incorporated check valve connected to the bag body 172.

As illustrated in FIG. 4, one end portion side of the tube 171, which is connected to the pressing portion 160, penetrates the band portion 130. An interlock member 138 configured to interlock with or be connected to the tube 171 is attached to the band portion 130. The tube 171 may directly interlock with the band portion 130 by welding without interposing a member such as the interlock member 138 between the tube 171 and the band portion 130.

To inflate (expand) the inflatable member 161 of the pressing portion 160, the operator inserts a distal tubular portion of a syringe into the connector 173 so as to open the check valve. A plunger of the syringe is pressed, and the air contained inside the syringe is injected into the inflatable space 163 via the injection portion 170. If the inflatable member 161 is inflated by this operation, the bag body 172 communicating with the inflatable space 163 via the tube 171 is expanded. The operator confirms the expansion of the bag body 172. In this manner, the operator can visually and easily confirm that the inflatable member 161 can be pressurized without leakage of the air.

The operator removes the distal tubular portion of the syringe from the connector 173 after injecting the air into the inflatable member 161. In addition, the operator can close the bag body 172 by using the check valve incorporated in the connector 173, and can prevent air leakage.

As illustrated in FIGS. 2 and 4, at a location for covering the pressing portion 160, the band portion 130 has the visually identifiable marker portion 136 for aligning the pressing portion 160 so as to overlap the site where bleeding is to be stopped t1.

As illustrated in FIG. 2, the marker portion 136 is disposed at a substantially central position in a plane direction of the pressing portion 160. In addition, as illustrated in FIG. 4, the marker portion 136 may be disposed on the inner surface of the band portion 130.

As illustrated in FIG. 2, the marker portion 136 may be formed in a rectangular shape in a plan view. However, a shape of the marker portion 136 is not particularly limited. For example, the shape of the marker portion 136 may be a circular shape, a triangular shape, a quadrangular shape, a star shape, or a pentagon shape.

In addition, a material forming the marker portion 136 is not particularly limited. For example, the material includes an oily coloring agent such as ink, or a resin mixed with a dye.

In addition, the color of the marker portion 136 is not particularly limited as long as the color enables the pressing portion 160 to align with the site where bleeding is to be stopped t1. However, it is preferable to use a green color system. Since the green color system is used, the operator can easily and visually confirm the marker portion 136 on the blood or the skin. Accordingly, the pressing portion 160 is much likely to align with the site where bleeding is to be stopped t1.

In addition, it is preferable that the marker portion 136 is translucent or colored transparent. In this manner, even in a state where the marker portion 136 overlaps the site where bleeding is to be stopped t1, the operator can visually confirm the site where bleeding is to be stopped t1 from the outer surface side of the marker portion 136.

A method of disposing the marker portion 136 in the band portion 130 is not particularly limited. For example, the method includes a method of printing the marker portion 136 on the band portion 130, a method of welding the marker portion 136 to the band portion 130, a method of affixing the marker portion 136 to the band portion 130 by applying an adhesive to one side surface of the marker portion 136.

The marker portion 136 may be disposed on the outer surface of the band portion 130. In addition, the marker portion 136 may be disposed in the inflatable member 161 of the pressing portion 160. In this case, it is preferable that the marker portion 136 is disposed on the inner surface side of the inflatable member 161 so that the marker portion 136 is not in direct contact with the site where bleeding is to be stopped t1 (refer to FIG. 4).

Next, a hemostatic method according to the present embodiment will be described with reference to FIGS. 7 to 10.

Figure 7:
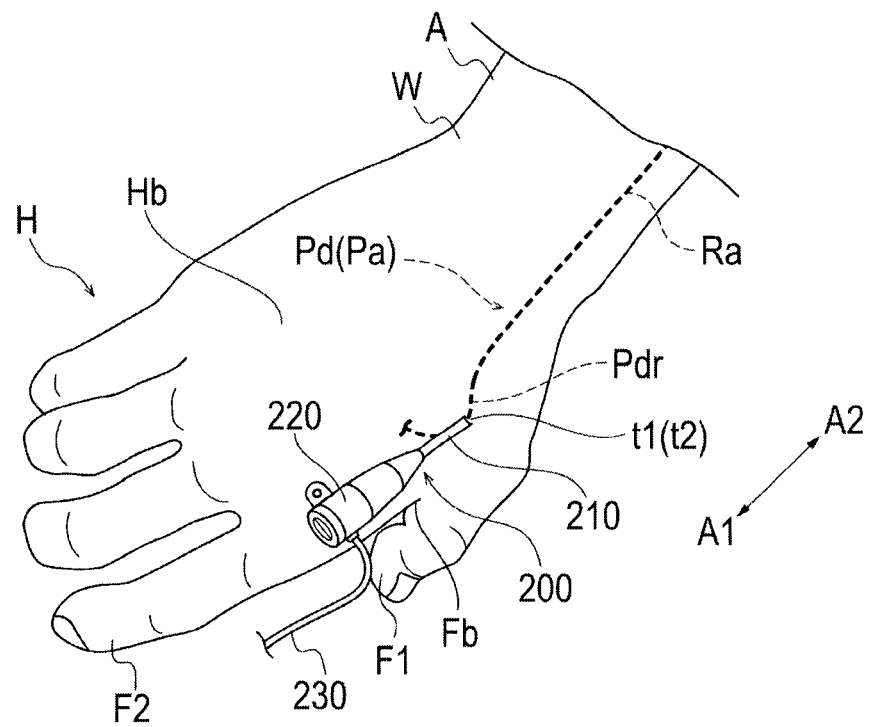
FIG. 7 is a perspective view for describing a wearing procedure and a hemostatic method of the hemostatic device according to the first embodiment.

As illustrated in FIG. 7, the operator inserts the sheath tube 210 of the introducer 200 into the radial artery side Pdr of the palmar artery Pa. Specifically, the operator uses a puncture needle known in the medical field to puncture a hole in the skin of the dorsal side Hb of the hand of the patient toward the radial artery side Pdr of the palmar artery Pa. As described above, in a state where the hand H of the patient is open, the puncture site t2 is formed between the center line c1 of the thumb F1 and the center line c2 of the forefinger F2 on the side of the dorsal side Hb of the hand side (refer to FIG. 6).

As illustrated in FIG. 7, as the introducer 200, it is possible to use an introducer including the sheath tube 210, a hub portion 220 disposed in a proximal portion of the sheath tube 210, a liquid injecting tube 230 for communicating with the lumen of the hub portion 220, and a dilator tube which can be inserted into and removed from the sheath tube 210.

Next, the operator inserts a guide wire into the radial artery side Pdr of the palmar artery Pa via the lumen of the puncture needle.

Next, the operator removes the puncture needle outward of the living body while the guide wire remains indwelled at the radial artery side Pdr of the palmar artery Pa.

Next, the operator inserts the dilator tube inserted into the sheath tube 210 into the radial artery side Pdr of the palmar artery Pa along the guide wire from the dorsal side Hb of the hand.

Next, as illustrated in FIG. 7, while the operator causes the sheath tube 210 to indwell the radial artery side Pdr of the palmar artery Pa, the operator removes the guide wire and the dilator tube from the radial artery side Pdr of the palmar artery Pa. Thereafter, the operator inserts medical devices such as a treatment instrument and a diagnostic instrument, the guide wire for delivering the medical devices to a blood vessel where a lesion area is present, into the radial artery side Pdr of the palmar artery Pa via the sheath tube 210.

The operator can insert the medical devices and the guide wire into a predetermined lesion area (for example, a stenosed site of the coronary artery) via the radial artery side Pdr of the palmar artery Pa, the radial artery Ra, and the brachial artery.

The operator removes the medical devices and the guide wire via the sheath tube 210 after completing treatment for the lesion area. In this case, the operator removes the medical devices and the guide wire outward of the living body through the brachial artery, the radial artery Ra, the radial artery side Pdr of the palmar artery Pa, and the puncture site t2 in this order.

Next, the operator uses the hemostatic device 100 to perform hemostasis.

As illustrated in FIG. 8, the operator disposes the band portion 130 of the covering portion 110 around the periphery of the site where bleeding is to be stopped t1 on the dorsal side Hb of the hand. In this case, the operator disposes a portion of the sheath tube 210 which is extracted outward of the living body so as to align with the indwelling portion 137 formed in the band portion 130 (refer to FIG. 5).

While the operator causes the sheath tube 210 of the introducer 200 to indwell the puncture site t2, the operator disposes the pressing portion 160 so as to overlap or overlie the puncture site t2 (refer to FIG. 4). In this case, while the operator visually confirms the marker portion 136 formed in the band portion 130, the operator disposes the marker portion 136 so as to overlap or overlie the site where bleeding is to be stopped t1. In this manner, the operator can easily align the pressing portion 160 with the puncture site t2.

In a working stage where the hemostatic device 100 is mounted on starts to be worn on the hand H, the hemostatic device 100 is in a state in which the pressing portion 160 is not inflated.

In a state where the band portion 130 is wrapped around the hand H, the operator joins the holding portions 140 (the male side 140a and the female side 140b of the surface fastener) to secure the band portion 130 to the hand H.

Figure 9:
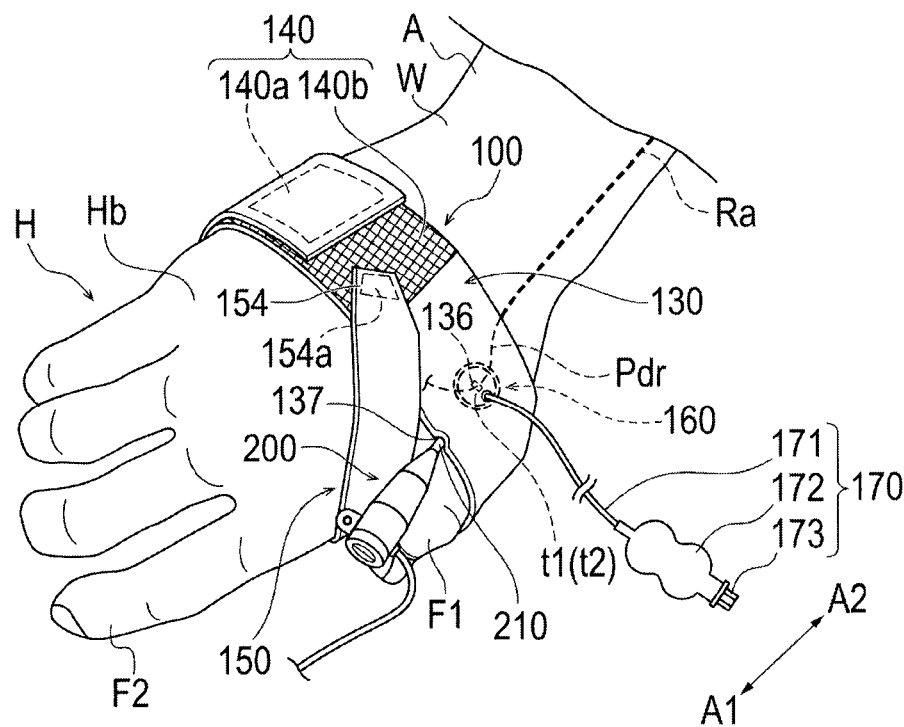
FIG. 9 is a perspective view for describing a wearing procedure and a hemostatic method of the hemostatic device according to the first embodiment.

Next, as illustrated in FIG. 9, the operator disposes the restriction portion 150 so that at least a portion of the restriction portion 150 is caught on the inter-finger portion Fb between the thumb F1 and the forefinger F2. In this case, the operator secures the male side 154a of the surface fastener disposed in the second end portion 154 of the restriction portion 150 to the holding portion 140 (female side 140b of the surface fastener).

As illustrated in FIG. 9, the operator causes the patient to wear the hemostatic device 100 on the hand H of the patient so that the injection portion 170 is directed to the downstream side (palm side) of the blood flow of the radial artery Ra. In this manner, when the injection portion 170 is operated, the operator can prevent an instrument (for example, a blood pressure monitor) located on the upstream side of the blood flow or the operator working on the upstream side of the blood flow and the injection portion 170 from interfering with each other. In a case of the radial artery Ra, the upstream side of the blood flow means a direction closer to the heart of the blood vessel, and the downstream side of the blood vessel means a direction away from the heart of the blood vessel. As shown in FIG. 9, as well as FIG. 2, the hemostatic device is configured so that when the hemostatic device 100 is worn on the patient's hand H (i.e., when the band portion is wrapped around the periphery of the patient's hand H at the site where bleeding is to be stopped while the restriction portion 150 passes between the thumb and the forefinger with the second end portion 154 of the restriction portion 150 interlocked with the band portion 130), the pressing portion 160 and the marker portion 136 are disposed on the thumb side of the band portion 130 between the first end portion 153 of the restriction portion and the second free end portion 154 of the restriction portion 150.

Next, the operator connects a syringe to the connector 173 of the injection portion 170, and injects the air into the pressing portion 160. The pressing portion 160 is inflated by injecting the air into the pressing portion 160 so as to apply the compressing force to the puncture site t2 formed on the radial artery side Pdr of the palmar artery Pa (refer to FIG. 4).

Figure 10:
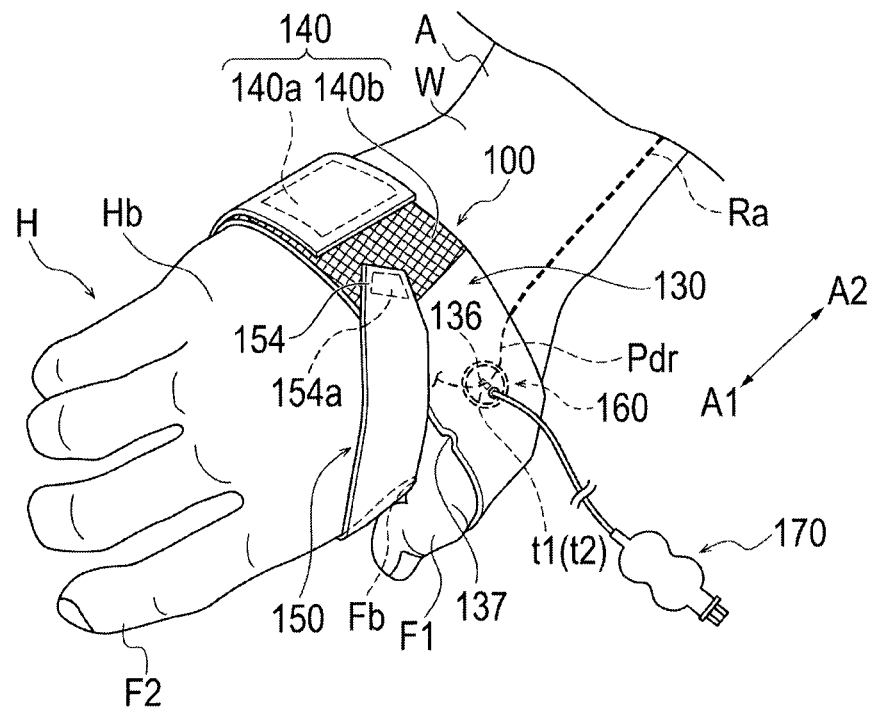
FIG. 10 is a perspective view for describing a wearing procedure and a hemostatic method of the hemostatic device according to the first embodiment.

As illustrated in FIG. 10, while maintaining the compressing force of the pressing portion 160 which is applied to the puncture site t2, the operator removes the sheath tube 210 of the introducer 200 from the puncture site t2.

In a state where the hemostatic device 100 is worn on the hand H of the patient, the puncture site t2 is disposed on the band portion 130 side from the restriction portion 150. In addition, in a state where the restriction portion 150 is disposed in the inter-finger portion Fb between the thumb F1 and the forefinger F2, the pressing portion 160 is disposed on the root side of the thumb from the second end portion 154 of the restriction portion 150.

After the pressing portion 160 is inflated so as to start the hemostasis, the operator can appropriately adjust the internal pressure of the pressing portion 160 in accordance with progress of the hemostasis. For example, in a case where the hemostasis is not sufficiently performed on the puncture site t2 after the pressing portion 160 is inflated, the operator can increase the internal pressure of the pressing portion 160 by injecting air again into the pressing portion 160. In addition, for example, in a case where the operator wants to return the internal pressure of the pressing portion 160 to the internal pressure of the pressing portion 160 into which the air is initially injected, the operator may inject the air as much as the amount of the air discharged from the pressing portion 160.

The patient can move the arm A, the wrist W, and the fingertip while the hemostasis is performed using the hemostatic device 100. Therefore, the patient can more freely move his or her body, compared to a case of the hemostasis in a state where the compressing force is applied to the puncture site formed on the arm or the wrist. Accordingly, QOL is improved.

The operator removes the hemostatic device 100 from the hand H after a predetermined time elapses and the hemostasis is completely performed on the puncture site t2. In this case, for example, after the operator releases the restriction portion 150 secured to the band portion 130, the operator releases the band portion 130 interlocked with the holding portion 140. In this manner, the operator can smoothly detach the hemostatic device 100.

An operation effect of the hemostatic device 100 and the hemostatic method according to the present embodiment will be described.

The hemostatic device 100 according to the present embodiment has the covering portion 110 disposed so as to cover the site where bleeding is to be stopped t1 on the hand H of the patient, and the pressing portion 160 that compresses the site where bleeding is to be stopped t1 in a state where the covering portion 110 covers the site where the bleeding is to be stopped t1. In addition, the covering portion 110 includes the securing portion 120 which surrounds at least a portion of the hand H of the patient while covering the pressing portion 160, and the restriction portion 150 which restricts the movement of the securing portion 120 in the axial direction. Then, the restriction portion 150 is disposed between the adjacent fingers F1 and F2 of the hand.

In a state where the covering portion 110 covers the site where bleeding is to be stopped t1 on the hand H of the patient, the above-described hemostatic device 100 can perform the hemostasis by causing the pressing portion 160 to compress the site where bleeding is to be stopped t1. Then, in a state where the hemostatic device 100 is worn on the hand H of the patient, while the hemostatic device 100 is secured by the securing portion 120 which surrounds the hand H, the movement in the axial direction (the extending direction of the fingers) is restricted by the restriction portion 150 disposed in the inter-finger portion Fb between the adjacent fingers F1 and F2 of the hand H. In this manner, the hemostatic device 100 can prevent a movable range of the fingers from being narrowed when the hemostatic device 100 is worn on the hand H, or to prevent misalignment in a state where the hemostatic device 100 is worn on the hand H.

In addition, the securing portion 120 of the hemostatic device 100 includes the band portion 130 wrapped around the site where bleeding is to be stopped t1 on the hand H, and the holding portion 140 which secures the band portion 130 in a state where the band portion 130 is wrapped around the periphery of the hand H. Then, in a state where the band portion 130 is wrapped around the periphery of the hand H, the restriction portion 150 is secured to the band portion 130 after passing through the inter-finger portion Fb between the thumb F1 and the forefinger F2.

According to the hemostatic device 100 configured as described above, the holding portion 140 stably maintains a state where the band portion 130 is wrapped around the periphery of the hand H. In addition, the restriction portion 150 is secured to the band portion 130 after passing through the inter-finger portion Fb between the thumb F1 and the forefinger F2. In this manner, the movement of the band portion 130 in the axial direction is restricted. Furthermore, the inter-finger portion Fb between the thumb F1 and the forefinger F2 has an area relatively larger than that of the inter-finger portion between other fingers. Accordingly, the operator can firmly hold the restriction portion 150 in the inter-finger portion Fb, and can preferably prevent the hemostatic device 100 from being misaligned.

In addition, the restriction portion 150 of the hemostatic device 100 has the first end portion 153 secured to the band portion 130, and the second end portion 154 facing the first end portion 153 and capable of freely detachably interlocking with the band portion 130. Then, in a state where the second end portion 154 interlocks with the band portion 130, the pressing portion 160 is disposed on the root side of the thumb F1 from the second end portion 154 of the restriction portion 150.

According to the hemostatic device 100 configured as described above, the second end portion 154 of the restriction portion 150 can be attached to and detached from the band portion 130. Accordingly, work for disposing the restriction portion 150 between the adjacent fingers of the patient is facilitated. In addition, the pressing portion 160 is disposed on the root side of the thumb F1 from the second end portion 154 of the restriction portion 150. Accordingly, in a state where the pressing portion 160 compresses the site where bleeding is to be stopped t1 (the puncture site t2), the pressing portion 160 may be prevented from being disposed on the fingertip side of the fingers. In this manner, the hemostatic device 100 may prevent the hand motion of the patient from being limited.

In addition, in the location for covering the pressing portion 160, the band portion 130 of the hemostatic device 100 has the marker portion 136 for aligning the pressing portion 160 so as to overlap the site where bleeding is to be stopped t1. According to the hemostatic device 100 configured in this way, the operator can rather easily align the pressing portion 160 with the site where bleeding is to be stopped t1. Therefore, a treatment time using the hemostatic device 100 can be shortened.

In addition, the restriction portion 150 of the hemostatic device 100 has a liquid absorbing layer 156 provided with a liquid absorbing property in a portion disposed on a surface layer side of the hand H of the patient. According to the hemostatic device 100 configured in this way, the liquid absorbing layer 156 absorbs (adsorbs) a body fluid such as the blood flowing to the restriction portion 150 side while the hemostasis is performed using the hemostatic device 100. Therefore, the operator can save time and labor in wiping the blood, and can shorten the treatment time using the hemostatic device 100.

In addition, the covering portion 110 of the hemostatic device 100 has the indwelling portion 137 which enables the sheath tube 210 of the introducer 200 to indwell the site where bleeding is to be stopped t1, between the pressing portion 160 and the restriction portion 150. According to the hemostatic device 100 configured in this way, the operator can cause the patient to wear the hemostatic device 100 on the hand H in a state where the sheath tube 210 of the introducer 200 remains indwelled, so that the wearing operation of the hemostatic device 100 can be easily and quickly performed.

The hemostatic method according to the present embodiment is used in performing the hemostasis on the puncture site t2 formed on the radial artery side Pdr of the palmar artery Pa of the patient. The hemostatic method includes providing the hemostatic device 100 including the covering portion 110 for covering the site where bleeding is to be stopped t1, which is present on the hand H of the patient, and the pressing portion 160 that compresses the site where bleeding is to be stopped t1, in a state where the covering portion 110 covers the site where bleeding is to be stopped t1, disposing the covering portion 110 around the site where bleeding is to be stopped t1, disposing the pressing portion 160 in the site where bleeding is to be stopped t1 so that the pressing portion 160 overlaps the puncture site t2, while the sheath tube 210 of the introducer 200 indwells the puncture site t2 formed on the hand H of the patient, securing the covering portion 110 to the hand H so that the puncture site t2 is compressed by the pressing portion 160, and removing the sheath tube 210 of the introducer 200 from the puncture site t2, while maintaining the compressing force applied to the puncture site t2 by the pressing portion 160.

According to the above-described hemostatic method, the hemostasis is performed on the puncture site t2 formed on the radial artery side Pdr of the palmar artery Pa of the patient, thereby preventing the motions of the arm A, the wrist W, and the fingertips of the patient from being limited while the hemostasis is performed. In this manner, the patient can more freely move his or her body. Accordingly, QOL is improved.

In addition, the covering portion 110 of the hemostatic device 100 used for the hemostasis includes the securing portion 120 which surrounds at least a portion of the hand H of the patient while covering the pressing portion 160, and the restriction portion 150 which restricts the movement of the securing portion 120 in the axial direction. Then, the restriction portion 150 is disposed between the adjacent fingers of the hand H in a state where the covering portion 110 is secured to the hand H so that the pressing portion 160 compresses the puncture site t2.

According to the above-described hemostatic method, in a state where the covering portion 110 covers the site where bleeding is to be stopped t1 on the hand H of the patient, the operator can perform the hemostasis by causing the pressing portion 160 to compress the site where bleeding is to be stopped t1. Then, in a state where the hemostatic device 100 is worn on the hand H of the patient, while the hemostatic device 100 is secured by the securing portion 120 surrounding the hand H, the movement in the axial direction (extending direction of the fingers) is restricted by the restriction portion 150 disposed between the adjacent fingers of the hand H. In this manner, the operator can prevent a movable range of the fingers of the patient wearing the hemostatic device 100, or can prevent misalignment of the hemostatic device 100.

In addition, the securing portion 120 of the hemostatic device 100 includes the band portion 130 wrapped around the site where bleeding is to be stopped t1 on the hand, and the holding portion 140 which secures the band portion 130 in a state where the band portion 130 wrapped around the periphery of the hand H. Then, in a state where the band portion 130 is wrapped around the periphery of the hand H, the restriction portion 150 is secured to the band portion 130 after passing through the inter-finger portion Fb between the thumb F1 and the forefinger F2.

According to the above-described hemostatic method, the operator can cause by the holding portion 140 to stably maintain a state where the band portion 130 is wrapped around the periphery of the hand H. In addition, the operator can prevent the misalignment of the hemostatic device 100 by using the restriction portion 150 disposed so as to pass through the inter-finger portion Fb having a relatively wide area between the thumb F1 and the forefinger F2.

In addition, in a state where the hand H of the patient is open, the puncture site t2 is formed between the center line c1 of the thumb F1 and the center line c2 of the forefinger F2 on the side of the dorsal side Hb of the hand. Then, in a state where the hemostatic device 100 is worn on the hand H of the patient, the puncture site t2 is disposed on the band portion 130 side from the restriction portion 150. According to this hemostatic method, the operator can cause the pressing portion 160 disposed in the band portion 130 to preferably apply the compressing force to the puncture site t2 formed on the radial artery side Pdr of the palmar artery Pa.

In addition, in a state where the restriction portion 150 is disposed between the adjacent fingers of the hand H of the patient, the pressing portion 160 is disposed on the root side of the thumb F1 from the second end portion 154 (end portion of the restriction portion 150 which is secured to the band portion 130) of the restriction portion 150. According to this hemostatic method, the operator can apply the compressing force to the puncture site t2 on the root side of the thumb F1. Therefore, it is possible to further widen the movable range of the hand H of the patient while the hemostasis is performed.

Next, modification examples according to the above-described first embodiment will be described. In the modification examples, configurations and materials which are not specifically described or medical procedures (procedures of the hemostatic method) which are not specifically described can be regarded as those according to the above-described embodiment, and so such description will not be repeated. In the description below of modification examples, features that are the same or similar to those described above are identified by the same reference numerals and a detailed description of such features is also not repeated.

Modification Example 1

Figure 11:
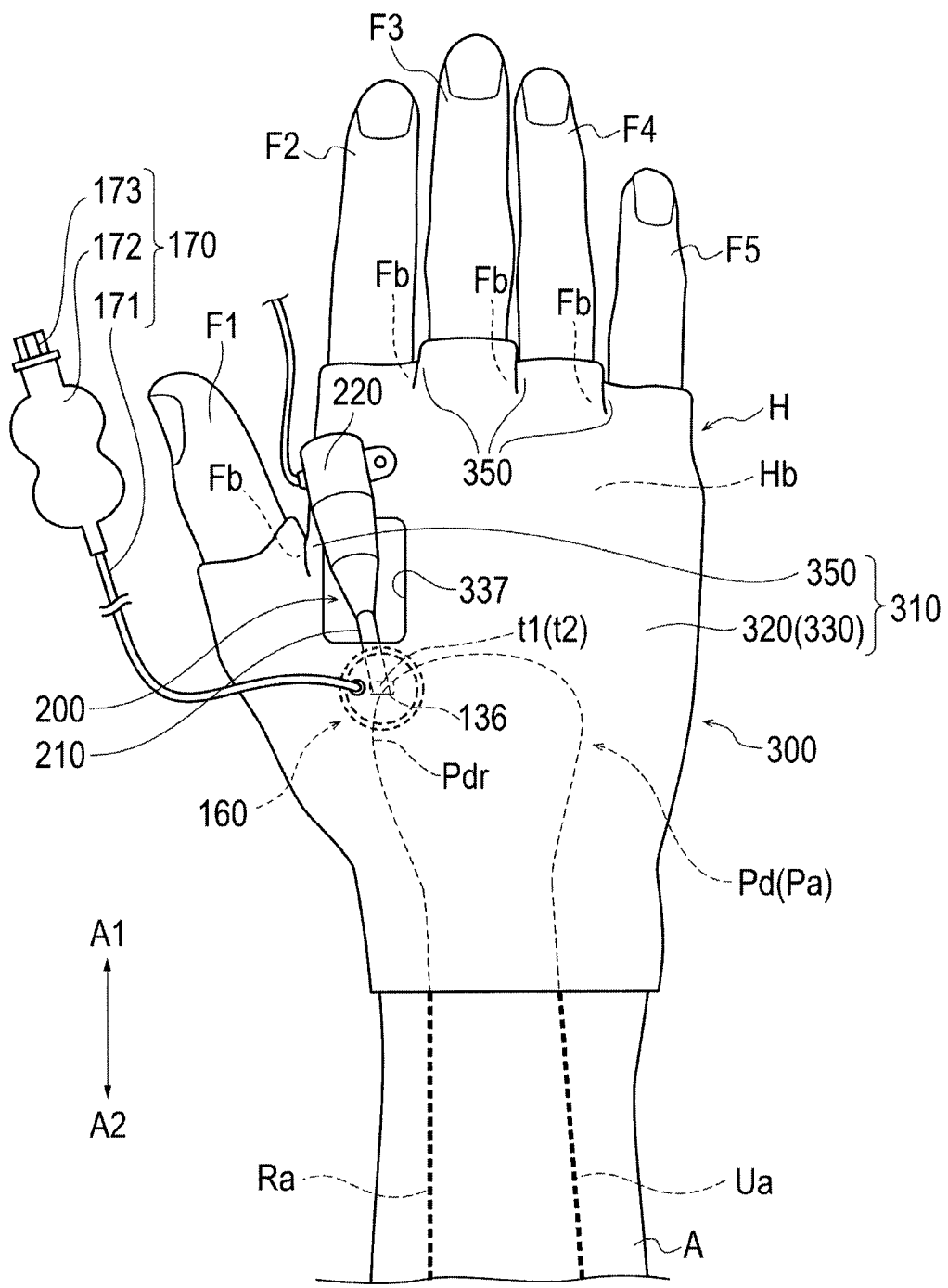
FIG. 11 is a plan view illustrating a state where a hemostatic device according to Modification Example 1 of the first embodiment is worn on the hand of the patient.

FIG. 11 is a plan view illustrating a state where a hemostatic device 300 according to Modification Example 1 is worn on the hand H of the patient, and FIG. 12 is a perspective view illustrating a state where the hemostatic device 300 according to Modification Example 1 is worn on the hand H of the patient. Note that, FIGS. 11 and 12 illustrate a state where the hemostatic device 300 is worn on the hand H of the patient in a state where the sheath tube 210 of the introducer 200 is indwelled at the hand H of the patient.

The hemostatic device 300 according to Modification Example 1 is configured so that a securing portion 320 and a restriction portion 350 which are included in a covering portion 310 have configurations different from those of the hemostatic device 100 according to the above-described first embodiment.

As illustrated in FIGS. 11 and 12, the securing portion 320 is configured to include a bag portion, surrounding portion or enclosure 330 which wraps around or surrounds (encircles) the whole dorsal side Hb of the hand while being in contact with the surface of the dorsal side Hb of the hand and while allowing exposure of part of the fingers. In addition, in a state where the bag portion 330 is wrapped around the dorsal side Hb of the hand, the restriction portion 350 is integrally formed in one piece with the bag portion 330 to pass between the adjacent fingers of the hand H.

The bag portion or enclosure 330 configuring or constituting the securing portion 320 has a structure such as a glove which covers the whole hand H of the patient. In addition, the bag portion 330 is formed in a shape so as to cover a certain range on the fingertip side from the inter-finger portion Fb between the respective fingers F1 to F5 and the root portions of the respective fingers F1 to F5. In other words, the bag portion 330 or enclosure is configured to extend from the inter-finger portion Fb between the respective fingers F1 to F5, along a portion of each of the fingers F1-F5, toward the free ends of the fingers F1-F5.

As illustrated in FIG. 11, the bag portion 330 has an indwelling portion 337 which enables the sheath tube 210 of the introducer 200 to indwell the site where bleeding is to be stopped t1.

The indwelling portion 337 is configured to include a through opening or an opening portion (hole portion) formed in the bag portion 330. The indwelling portion 337 exposes a portion of the dorsal side Hb of the hand from the bag portion 330. In a state where the bag portion 330 wraps or is wrapped around the dorsal side Hb of the hand, the indwelling portion 337 is disposed between the thumb F1 of the hand and the forefinger F2 of the hand (position where at least a portion of the indwelling portion 337 is disposed between the extension line of the thumb F1 of the hand and the extension line of the forefinger of the hand).

In addition, in a state where the bag portion 330 wraps or is wrapped around the dorsal side Hb of the hand, the indwelling portion 337 is disposed on the thumb F1 side (fingertip side of the thumb F1) from the pressing portion 160. In other words, the through hole defining the indwelling portion 337 is positioned between the pressing portion 160 and the base side of the forefinger F2 (the end of the enclosure 330 covering a portion of the forefinger F2).

The pressing portion 160 is disposed on the inner surface (surface facing a surface layer of the dorsal side Hb of the hand) of the bag portion 330. A structure of the pressing portion 160 can adopt a configuration substantially the same as that of the above-described hemostatic device 100. In addition, for example, the liquid absorbing layer capable of absorbing the body fluid such as the blood can be disposed at any desired position on the inner surface of the bag portion 330.

For example, the bag portion 330 can be formed of a material the same as that of the band portion 130 according to the above-described embodiment. In the bag portion 330, it is preferable that at least a portion which overlaps the pressing portion 160 is transparent, translucent, or colored transparent.

Next, a procedure for using the hemostatic device 300 according to Modification Example 1 will be described.

Figure 12A:
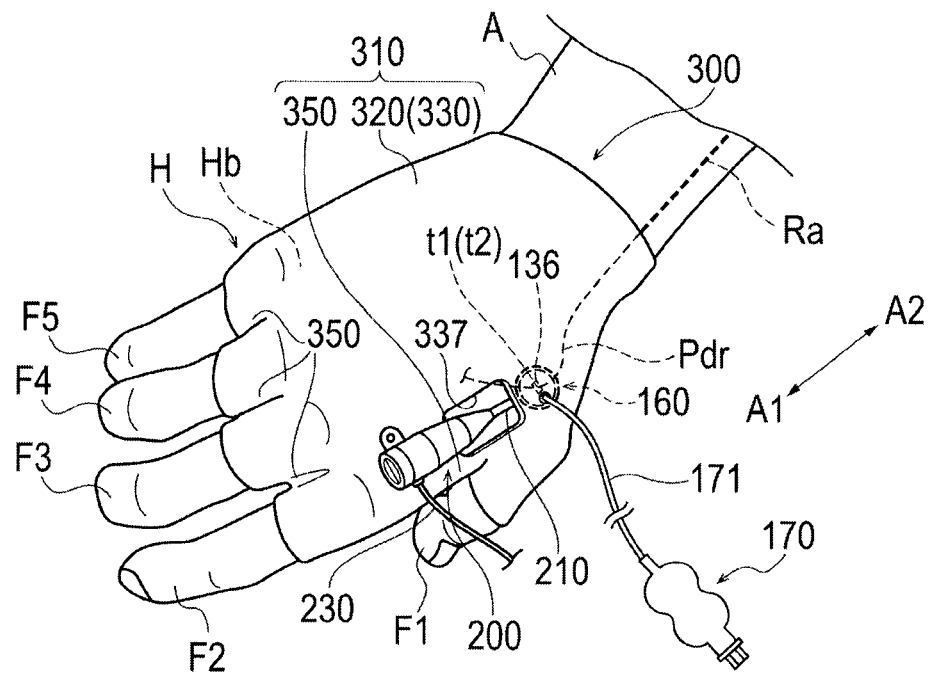
FIGS. 12(A) and 12(B) are perspective views illustrating a state where the hemostatic device according to Modification Example 1 of the first embodiment is worn on the hand of the patient.
Figure 12B:
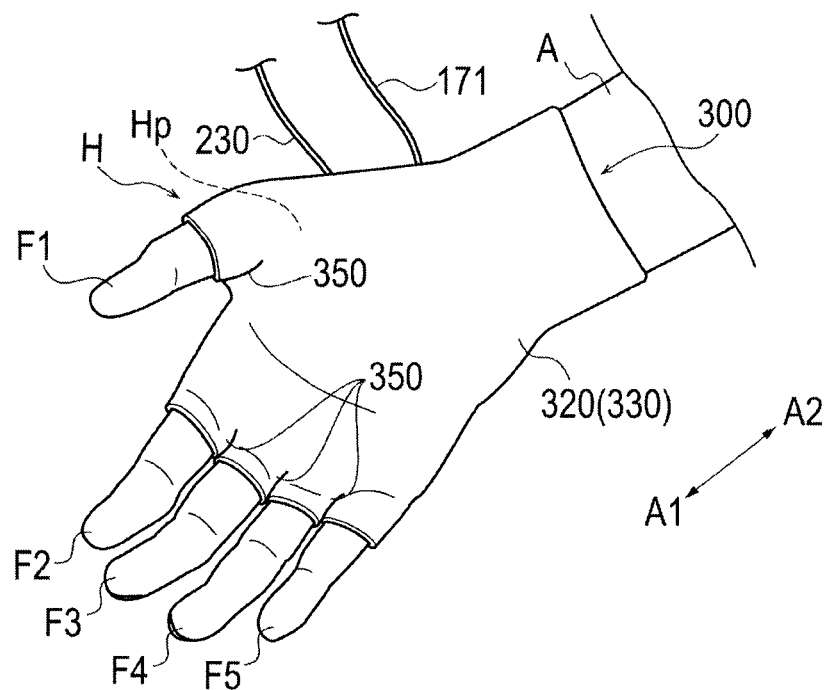

As illustrated in FIGS. 12(A) and 12(B), while the operator causes the sheath tube 210 of the introducer 200 to indwell the radial artery side Pdr of the palmar artery Pa, the operator covers the hand H of the patient with the bag portion or enclosure 330 of the hemostatic device 300. Specifically, the operator covers the dorsal side Hb of the hand and the palm Hp side with the bag portion 330 from the fingertip side of the hand H. In this case, the operator causes the introducer 200 to pass through the indwelling portion 337 of the bag portion 330. In this manner, the hand H can be covered with the bag portion 330 without causing interference between the introducer 200 and the bag portion 330.

After the hemostatic device 300 is worn on the hand H of the patient, the operator connects a syringe (not illustrated) to the connector 173 of the injection portion 170, and injects the air into the pressing portion 160. The pressing portion 160 is inflated by the injected air, and the compressing force is applied to the puncture site t2 formed on the radial artery side Pdr of the palmar artery Pa.

In a state where the hub portion 220 of the introducer 200 is extracted from the indwelling portion 337, the operator can maintain the sheath tube 210 in a state of indwelling the puncture site t2.

Next, while maintaining the compressing force of the pressing portion 160 which is applied to the puncture site t2, the operator removes the sheath tube 210 of the introducer 200 from the puncture site t2. In this case, the operator causes the introducer 200 to pass through the indwelling portion 337 of the bag portion 330. In this manner, the operator can remove the sheath tube 210 from the puncture site t2 so that the introducer 200 does not interfere with the bag portion 330.

An operation effect of the hemostatic device 300 according to this modification example will be described.

The securing portion 320 included in the hemostatic device 300 according to this modification example is configured to include the bag portion 330 which surrounds the whole dorsal side Hb of the hand while being in contact with the surface of the dorsal side Hb of the hand of the patient. Then, the restriction portion 350 is formed integrally with the bag portion 330 so as to pass between the adjacent fingers of the hand H, in a state where the bag portion 330 wraps the dorsal side Hb of the hand.

The hemostatic device 300 configured as described above has the bag portion 330 disposed so as to come into contact with the dorsal side Hb of the hand of the patient. Accordingly, it is possible to improve a securing force of the hemostatic device 300 which is applied to the hand H of the patient. In addition, in the hemostatic device 300, the restriction portion 350 is formed integrally with the bag portion 330. Therefore, the operator can dispose the restriction portion 350 between the adjacent fingers by causing the bag portion 330 to be worn on the dorsal side Hb of the hand of the patient. In this manner, the operator enables the hemostatic device 300 to be easily worn on the hand H of the patient.

In addition, the bag portion 330 of the hemostatic device 300 has the indwelling portion 337 which enables the sheath tube 210 of the introducer 200 to indwell the site where bleeding is to be stopped t1. In a state where the bag portion 330 wraps or is wrapped around the dorsal side Hb of the hand of the patient, the indwelling portion or through hole 337 is disposed between the thumb F1 of the hand and the forefinger F2 of the hand. Therefore, in a state where the bag portion 330 is worn on the dorsal side Hb of the hand, the operator can stably maintain a state where the sheath tube 210 of the introducer 200 is indwelled at the puncture site t2.

In addition, in a state where the bag portion 330 wraps or is wrapped around the dorsal side Hb of the hand, the indwelling portion 337 or through hole of the hemostatic device 300 is disposed on the thumb F1 side from the pressing portion 160. Therefore, the operator can dispose the hub portion 220 of the introducer 200 on the thumb F1 side, and can dispose the introducer 200 toward the fingertip side of the fingers. This enables the operator to relatively easily operate the introducer 200 even in a state where the hemostatic device 300 is worn on the hand H of the patient.

The number of the restriction portions 350 disposed in the hemostatic device 300 according to Modification Example 1 and the number of the fingers which can be simultaneously covered with the bag portion or enclosure 330 are not particularly limited.

Modification Example 2

Figure 13:
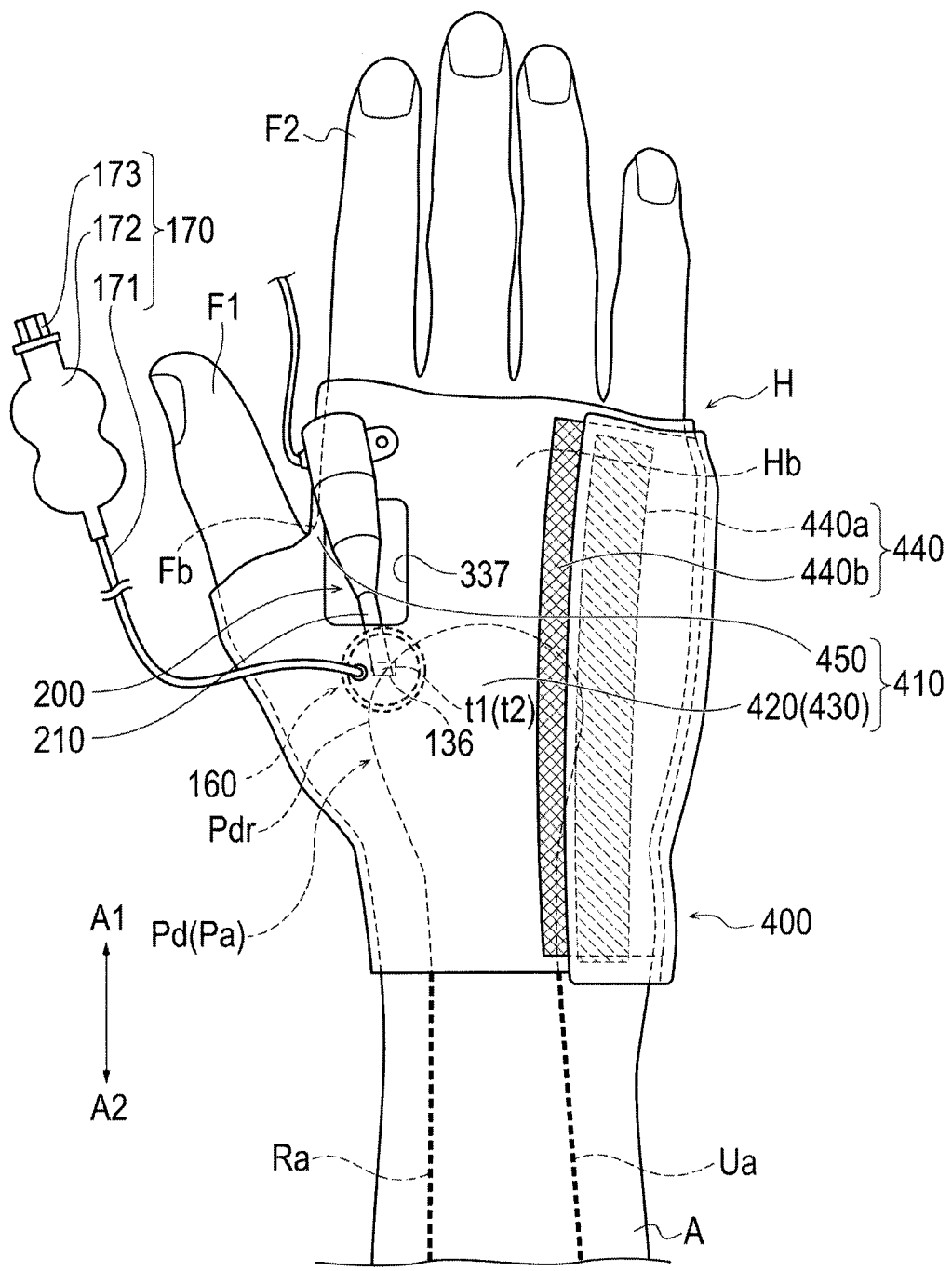
FIG. 13 is a plan view illustrating a state where a hemostatic device according to Modification Example 2 of the first embodiment is worn on the hand of the patient.
Figure 14A:
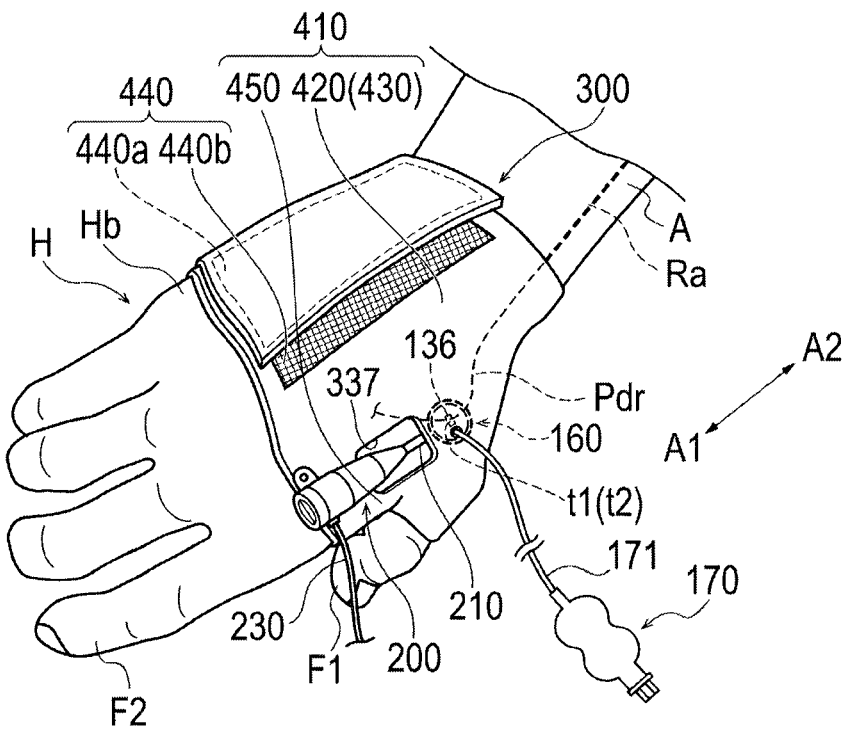
FIGS. 14(A) and 14(B) are perspective views illustrating a state where the hemostatic device according to Modification Example 2 of the first embodiment is worn on the hand of the patient.
Figure 14B:
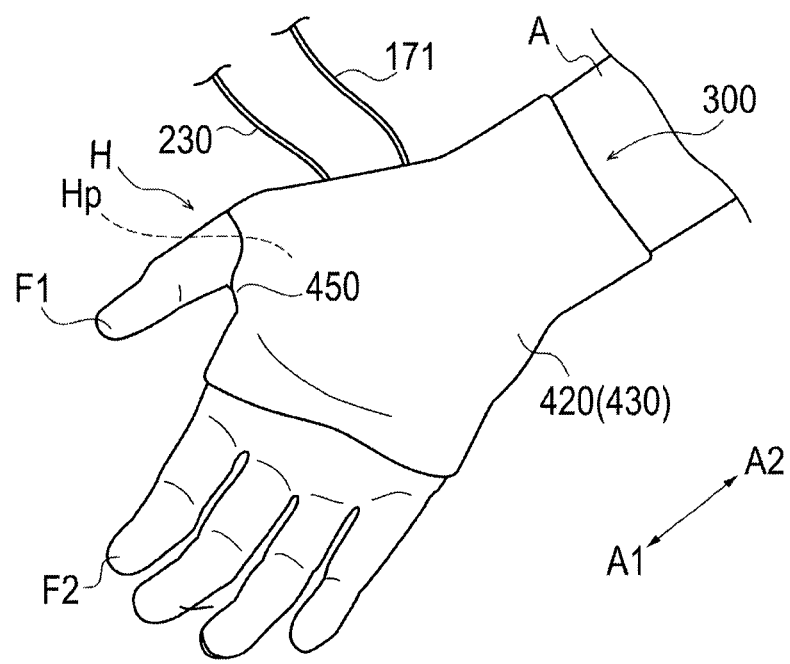

FIG. 13 is a plan view illustrating a state where a hemostatic device 400 according to Modification Example 2 is worn on the hand H of the patient. FIG. 14 is a perspective view illustrating a state where the hemostatic device 400 according to Modification Example 2 is worn on the hand H of the patient. FIGS. 13 and 14 illustrate the hemostatic device 400 worn on the hand H of the patient in a state where the sheath tube 210 of the introducer 200 indwells or is indwelled in the hand H of the patient.

In the hemostatic device 400 according to Modification Example 2, a configuration of a securing portion 420 (bag portion 430) configured to wrap the dorsal side Hb of the hand of the patient differs from that of the hemostatic device 300 according to Modification Example 1.

As illustrated in FIGS. 13 and 14, the bag portion or enclosure 430 is configured to be wrapped around, surround or enclose (surround) the hand H of the patient. The bag portion 430 has a holding portion 440 for maintaining a state where the bag portion 430 is wrapped around the hand H.

The holding portion 440 has a male side 440a (or a female side 440b) of the surface fastener formed in the bag portion 430 and a female side 440b (or a male side) of the surface fastener.

The operator joins the male side 440a of the surface fastener and the female side 440b of the surface fastener to each other. In this manner, the operator can maintain a state where the bag portion 430 is wrapped around the hand H of the patient. In addition, the operator releases the male side 440a of the surface fastener which is joined to the female side 440b of the surface fastener. In this manner, the operator can release the state where the bag portion 430 is wrapped around the hand H of the patient (e.g., to remove the hemostatic device 400 from the patient's hand).

The holding portion 440 may be a snap, a button, a clip, or a frame member passing through the end portion of the bag portion 330, for example.

The bag portion 430 is formed so as to partially cover the root side of the thumb F1 in the hand H of the patient. A restriction portion 450 is formed integrally with the bag portion 430, and is disposed in the inter-finger portion Fb between the thumb F1 and the forefinger F2, in a state where the bag portion 430 is wrapped around the dorsal side Hb of the hand of the patient.

The bag portion 330 of the hemostatic device 300 according to Modification Example 1 described above is formed so as to partially cover the root side of the respective fingers F1 to F5. However, the hemostatic device 400 according to Modification Example 2 is formed so that the fingers other than the thumb F1 are exposed. That is, the bag portion or enclosure 330 is configured to entirely encircle the base of the thumb F1, by virtue of the restriction portion 450, but the other fingers F2-F5 are not similarly entirely encircled. In Modification Example 1 shown in FIGS. 11, 12A and 12B, a part of the bag portion or enclosure 330 entirely encircles the base of each of the fingers F1-F5.

Similarly to the hemostatic device 300 according to Modification Example 1 described above, the hemostatic device 400 according to Modification Example 2 has the improved securing force applied to the hand H of the patient. In addition, in the hemostatic device 400, the restriction portion 450 is formed integrally with the bag portion 430. Therefore, the operator causes the bag portion 430 to be worn on the dorsal side Hb of the hand of the patient. In this manner, the operator can dispose the restriction portion 450 between the adjacent fingers. In this manner, the operator enables the hemostatic device 400 to be easily worn on the hand H of the patient.

Furthermore, the operator uses the holding portion 440 formed in the bag portion 430. In this manner, the operator enables the bag portion 430 to be easily worn on the hand H of the patient, and enables the bag portion 430 to be easily detached from the hand H of the patient.

The holding portion 440 described in the hemostatic device 400 according to Modification Example 2 can also be disposed in the bag portion 330 of the hemostatic device 300 according to Modification Example 1 described above.

Modification Example 3

Figure 15:
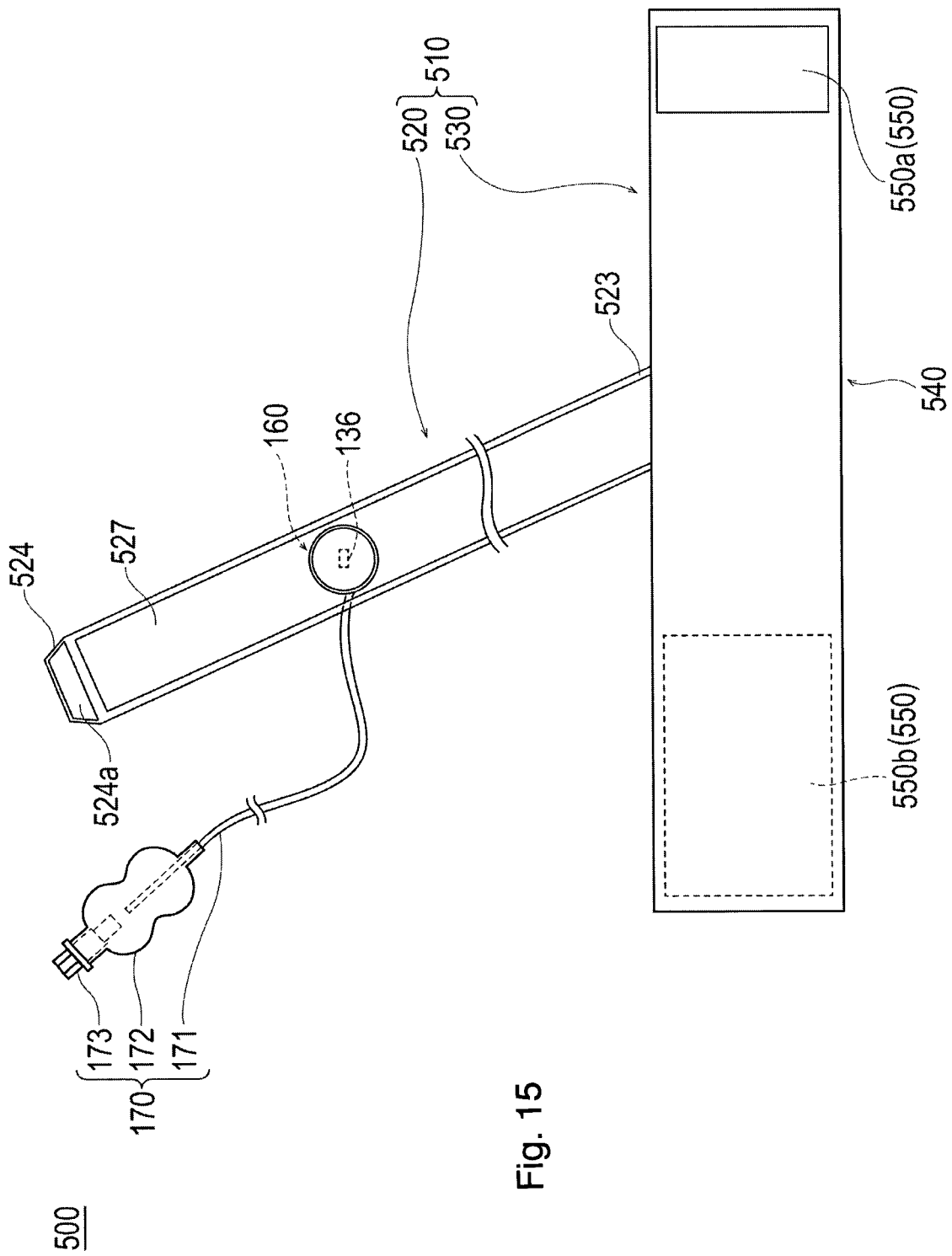
FIG. 15 is a plan view when a hemostatic device according to Modification Example 3 of the first embodiment is viewed from the inner surface side.
Figure 16:
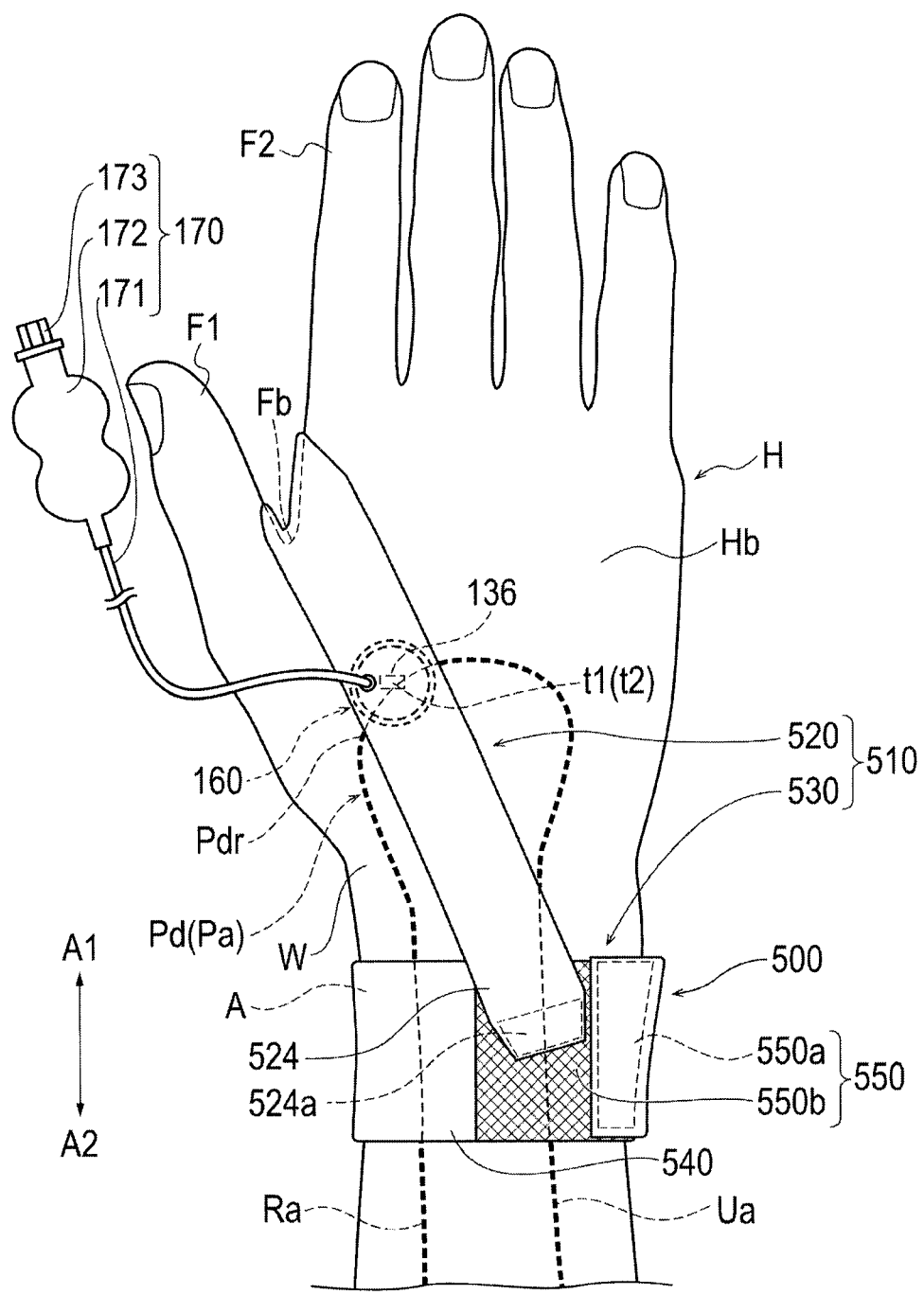
FIG. 16 is a plan view illustrating a state where the hemostatic device according to Modification Example 3 of the first embodiment is worn on the hand of the patient.

FIG. 15 is a plan view when a hemostatic device 500 according to Modification Example 3 is viewed from the inner surface side. FIG. 16 is a plan view illustrating a state where the hemostatic device 500 according to Modification Example 3 is worn on the hand H of the patient, and FIG. 17 is a perspective view illustrating the state where the hemostatic device 500 according to Modification Example 3 is worn on the hand H of the patient.

In the hemostatic device 500 according to Modification Example 3, the configuration of the securing portion 520 and the restriction portion 530 which are included in or form a part of the covering portion 510 differ from that of the hemostatic device 100 according to the above-described first embodiment.

As illustrated in FIGS. 15 and 16, the covering portion 510 of the hemostatic device 500 includes the securing portion 520 which covers the pressing portion 160, and the restriction portion 530 which surrounds the arm A (or the wrist W) of the patient while restricting the movement of the securing portion 520.

Figure 17A:
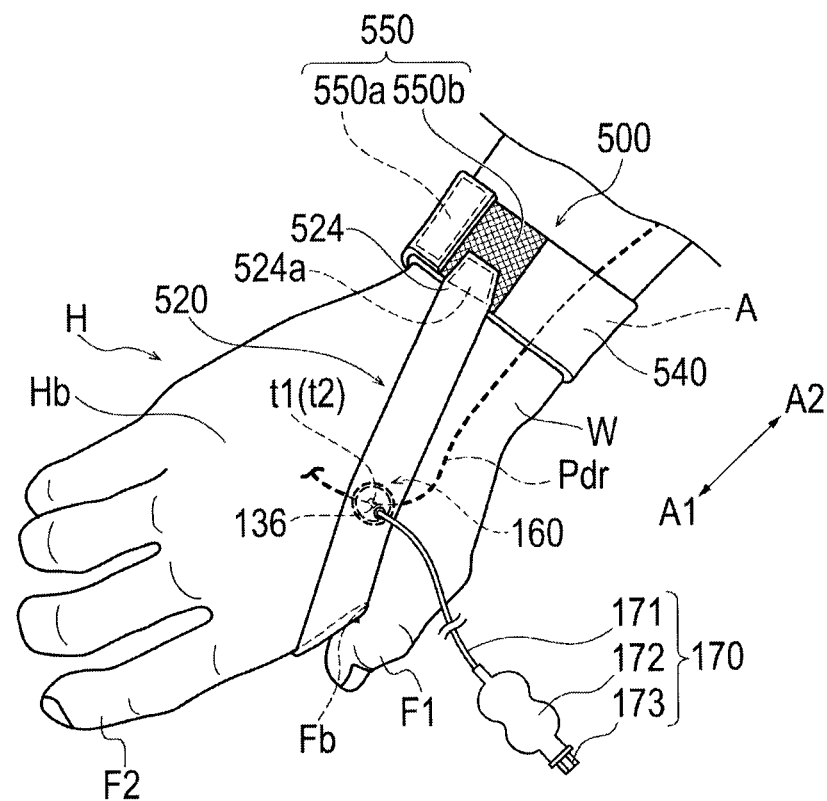
FIGS. 17(A) and 17(B) are perspective views illustrating a state where the hemostatic device according to Modification Example 3 of the first embodiment is worn on the hand of the patient.
Figure 17B:
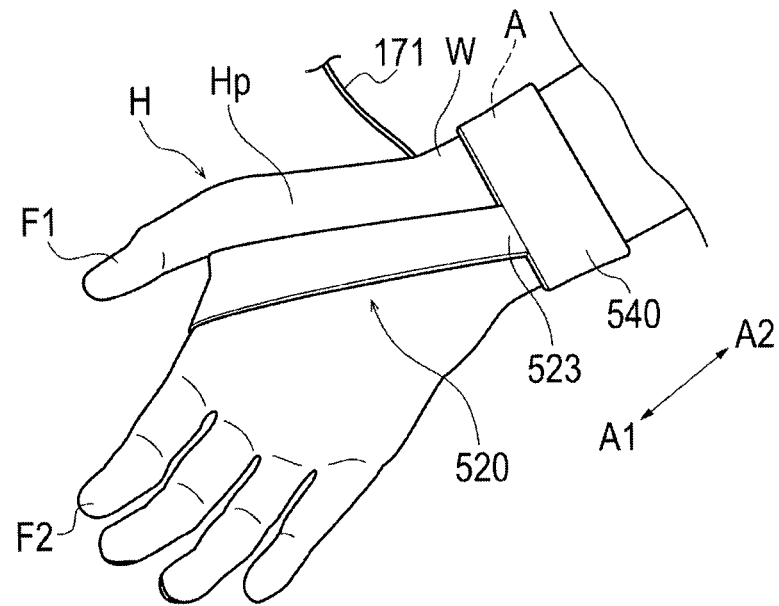

As illustrated in FIGS. 16 and 17, the restriction portion 530 includes a band portion 540 wrapped around the arm A of the patient, and a holding portion 550 which secures the band portion 540 in a state where the band portion 540 is wrapped around the arm A of the patient.

The band portion 540 can be formed to be substantially the same as the band portion 130 of the above-described hemostatic device 100. However, for example, the band portion 540 can be formed to have the length of 60 mm to 600 mm, and can be formed to have the width of 3 mm to 500 mm so that the band portion 540 can be wrapped around the arm A.

As illustrated in FIG. 15, the holding portion 550 has a male side (or a female side) 550a of the surface fastener disposed on the inner surface side of the band portion 540, and a female side (or a male side) 550b of the surface fastener disposed on the outer surface side of the band portion 540.

As illustrated in FIGS. 16 and 17, in a state where the band portion 540 is wrapped around the periphery of the arm A, the securing portion 520 is secured to the band portion 540 after passing through the inter-finger portion Fb between the thumb F1 and the forefinger F2.

As illustrated in FIGS. 16 and 17, the securing portion 520 has a first end portion 523 secured to the band portion 540, and a second end portion 524 facing the first end portion 523 and capable of freely detachably interlocking with the band portion 540.

As illustrated in FIG. 15, in a state where the second end portion 524 is separated from the band portion 540, the securing portion 520 extends while being inclined at a predetermined angle in the extending direction (rightward-leftward direction in FIG. 15) of the band portion 540. That is, as illustrated, the securing portion 520 extends at an oblique angle relative to the direction of extent of the band portion 540.

By way of example, the securing portion 520 can have a length in the extending direction of 50 mm to 5000 mm, and can be formed to have the width of 3 mm to 60 mm. The width of the securing portion 520 is a dimension in a direction orthogonal to the extending direction (longitudinal direction) of the securing portion 520.

The male side (or the female side) 524a of the surface fastener is disposed in the second end portion 524 of the securing portion 520. As illustrated in FIG. 16, the operator joins the male side 524a of the surface fastener of the securing portion 520 and the female side 550b of the surface fastener of the band portion 540 to each other. In this manner, the operator can interlock the securing portion 520 with the band portion 540.

As illustrated in FIG. 15, the securing portion 520 has a liquid absorbing layer 527 having the liquid absorbing property in a portion (inner surface of the securing portion 520) disposed on the surface layer side of the hand H. The liquid absorbing layer 527 can be substantially the same as the liquid absorbing layer 156 of the above-described hemostatic device 100.

As illustrated in FIG. 15, the pressing portion 160 is disposed on the inner surface of the securing portion 520. The pressing portion 160 can be substantially the same as the pressing portion of the above-described hemostatic device 100.

By way of example, the inner surface of the securing portion 520 can have the indwelling portion 137 (refer to FIG. 4) configured to include a concave groove. In addition, for example, the inner surface of the securing portion 520 may have an adhesive layer (sealing member) around the pressing portion 160 in order to more reliably prevent the securing portion 520 from being misaligned with the hand H of the patient.

In addition, for example, the securing portion 520 and the band portion 540 can be formed of a material the same as that of the band portion 130 according to the above-described embodiment. In the securing portion 520, it is preferable that at least a portion which overlaps the pressing portion 160 is formed to be transparent, translucent, or colored transparent.

For example, the securing portion 520 may be configured to be disposed between fingers other than the thumb F1 and the forefinger F2. In addition, for example, a plurality of the securing portions 520 may be disposed in one hemostatic device 500. In this case, the securing portion 520 may be formed so as to have a plurality of portions divided from the securing portion 520 and disposed between different fingers. Alternatively, the securing portion 520 may be formed so as to have a plurality of portions divided from the band portion 540 and disposed between different fingers. In addition, for example, the securing portion 520 may be formed integrally with the band portion 540 so that the securing portion 520 cannot be attached to and detached from the band portion 540. By way of example, in a case where the securing portion 520 has the plurality of portions disposed between the respective fingers, some may be attachable to and detachable from the band portion 540, and some may not be attachable to and detachable from the band portion 540.

Next, a procedure for using the hemostatic device 500 according to Modification Example 3 will be described.

While the operator causes the sheath tube 210 of the introducer 200 to indwell the radial artery side Pdr of the palmar artery Pa (refer to FIG. 8), the operator secures the band portion 540 by wrapping the band portion 540 around the arm A of the patient.

Next, in a state where the band portion 540 is wrapped around the arm A of the patient, the operator secures the band portion 540 to the inter-finger portion Fb between the thumb F1 and the forefinger F2 of the hand H of the patient through the securing portion 520. In this case, the operator disposes the pressing portion 160 disposed in the securing portion 520 so as to overlap the site where bleeding is to be stopped t1 on the hand.

Next, the operator connects the syringe to the connector 173 of the injection portion 170, and injects the air into the pressing portion 160. The pressing portion 160 is inflated by injecting the air into the pressing portion 160 to apply the compressing force to the puncture site t2 formed on the radial artery side Pdr of the palmar artery Pa (refer to FIG. 4).

While maintaining the compressing force of the pressing portion 160 which is applied to the puncture site t2, the operator removes the sheath tube 210 of the introducer 200 from the puncture site t2.

The patient can move his or her elbows or fingers while the hemostatic device 500 performs the hemostasis. Therefore, the patient can more freely move his or her body, compared to a case of the hemostasis in a state where the compressing force is applied to the puncture site formed on the arm or the wrist. Accordingly, QOL is improved.

The operator removes the hemostatic device 500 from the arm A of the patient after a predetermined time elapses and the hemostasis is completely performed on the puncture site t2. In this case, for example, after the operator releases the securing portion 520 secured to the band portion 540, the operator releases the band portion 540 interlocked with the holding portion 550. In this manner, the operator can easily detach the hemostatic device 100.

As described above, the hemostatic device 500 according to this modification example has the covering portion 510 disposed so as to cover the site where bleeding is to be stopped t1 on the hand H of the patient, and the pressing portion 160 which compresses the site where bleeding is to be stopped t1 while the covering portion 510 covers the site where bleeding is to be stopped t1. In addition, the covering portion 510 includes the securing portion 520 which covers the pressing portion 160, and the restriction portion 530 which surrounds the arm A of the patient while restricting the movement of the securing portion 520. Then, the securing portion 520 is disposed between the adjacent fingers of the hand H of the patient.

While the above-described hemostatic device 500 performs the hemostasis by causing the securing portion 520 disposed between the adjacent fingers F1 and F2 of the hand H of the patient to secure the pressing portion 160 to the hand H of the patient, the above-described hemostatic device 500 causes the restriction portion 530 surrounding the arm A of the patient to restrict the movement of the securing portion 520 in the axial direction. In this manner, the hemostatic device 100 can prevent a movable range of the fingers from being narrowed when the hemostatic device 100 is worn on the hand H, or to prevent misalignment in a state where the hemostatic device 100 is worn on the hand H.

In addition, in the hemostatic device 500, the restriction portion 530 is disposed on the arm A having a relatively smaller movement amount (movable range) generated by the movement of the patient compared to the hand H. Accordingly, the securing portion 520 can be preferably prevented from moving in the axial direction.

In addition, the restriction portion 530 of the hemostatic device 500 includes the band portion 540 wrapped around the arm A of the patient, and the holding portion 550 which secures the band portion 540 in a state where the band portion 540 is wrapped around the arm A of the patient. Then, in a state where the band portion 540 is wrapped around the arm A of the patient, while the securing portion 520 compresses the site where the bleeding is to be stopped t1 on the hand, the securing portion 520 is secured to the band portion 540 after passing through the thumb F1 and the forefinger F2 of the hand H of the patient.

According to the hemostatic device 500 configured as described above, the holding portion 550 stably maintains a state where the band portion 540 is wrapped around the periphery of the arm A. In addition, the securing portion 520 is secured to the band portion 540 after passing through the inter-finger portion Fb between the thumb F1 of the hand and the forefinger F2 of the hand. In this manner, the movement of the band portion 540 in the axial direction is restricted. Furthermore, the inter-finger portion Fb between the thumb F1 and the forefinger F2 has a relatively wider area than the inter-finger portion between other fingers. Accordingly, the restriction portion 150 can be firmly held in the inter-finger portion Fb, and it is possible to more preferably prevent misalignment of the hemostatic device 500.

The hemostatic device 500 according to Modification Example 3 may be configured so that, for example, the restriction portion 530 surrounds the wrist W of the patient, or may be configured to partially cover a portion of the wrist W of the patient and a portion of the arm A.

Second Embodiment

Next, a hemostatic device 600 according to a second embodiment will be described. In the second embodiment, configurations and materials which are not specifically described or medical procedures (procedures of the hemostatic method) which are not specifically described are to be regarded as those according to the above-described first embodiment, and thus, the description of such features will not be repeated. In the description below, features that are the same or similar to those described above are identified by common reference numerals and a detailed description of such features is also not repeated.

Figure 18:
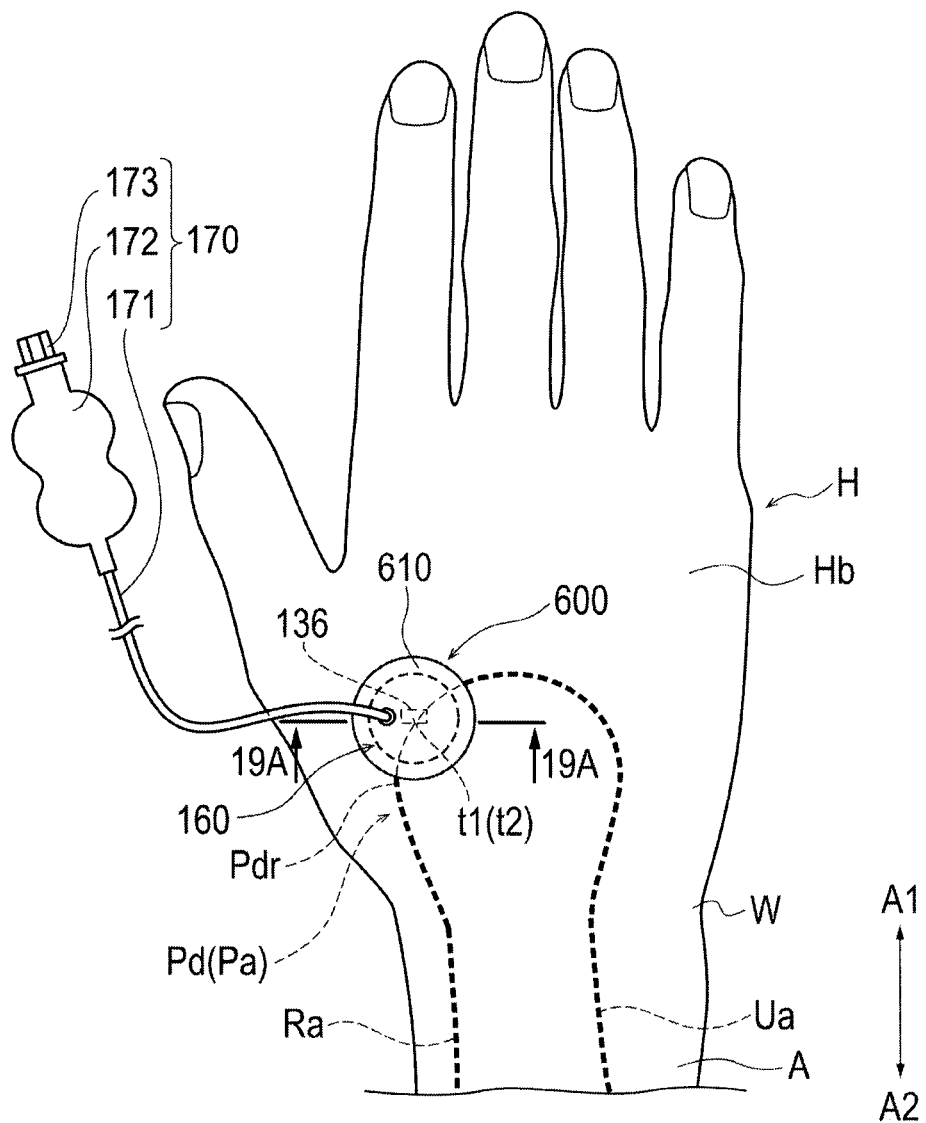
FIG. 18 is a plan view illustrating a state where a hemostatic device according to a second embodiment of the present invention is worn on the hand of the patient.
Figure 19:
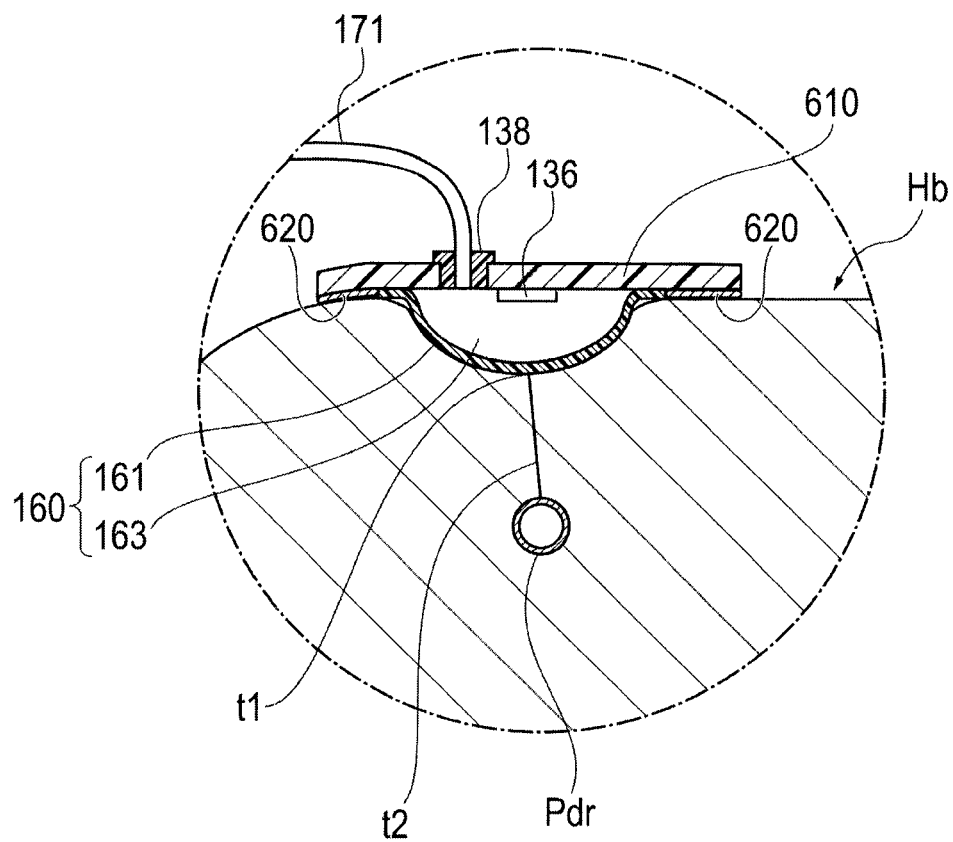
FIG. 19 is an enlarged view of a portion of a cross section taken along the arrow line 19A-19A illustrated in FIG. 18.

FIG. 18 is a plan view illustrating a state where the hemostatic device 600 according to the second embodiment is worn on the hand H of the patient, and FIG. 19 is an enlarged cross-sectional view illustrating a portion taken along line 19A-19A illustrated in FIG. 18.

In the hemostatic device 600 according to the second embodiment, the configuration of a covering portion 610 differs from that of the hemostatic device 100 according to the first embodiment.

As illustrated in FIGS. 18 and 19, the hemostatic device 600 has the covering portion 610 disposed so as to cover the site where bleeding is to be stopped t1 on the hand H of the patient, and the pressing portion 160 which compresses the site where bleeding is to be stopped t1 in a state where the covering portion 610 covers the site where bleeding is to be stopped t1.

As illustrated in FIG. 19, the covering portion 610 is formed from a sheet-like or sheet-shaped member which covers the site where bleeding is to be stopped t1. The pressing portion 160 is disposed on the inner surface of the covering portion 610. The pressing portion 160 is welded (or adhered) to the inner surface of the covering portion 610. The pressing portion 160 can be substantially the same as the pressing portion 160 of the hemostatic device 100 according to the first embodiment.

An adhesive layer 620 is disposed on the inner surface of the covering portion 610 so as to surround the periphery of the pressing portion 160. For example, it is preferable that the adhesive layer 620 is provided with a relatively strong securing force (adhesive force) so that the covering portion 610 can be stably maintained in a state where the covering portion is affixed to the hand H of the patient.

As illustrated in FIG. 18 and FIG. 19, the marker portion 136 is disposed on the inner surface of the covering portion 610. The marker portion 136 can be substantially the same as that of the hemostatic device 100 according to the first embodiment.

By way of example, the liquid absorbing layer capable of absorbing the body fluid such as the blood can be disposed around the pressing portion 160 on the inner surface of the covering portion 610.

In addition, the hemostatic device 600 may be provided with a protective member (protective sheet) that covers the adhesive layer 620 in a state where the hemostatic device 600 is not used. In a case where the hemostatic device 600 is configured in this way, when the hemostatic device 600 is used, the operator detaches the protective member from the adhesive layer 620. In this manner, the operator can secure the covering portion 610 to the hand H of the patient by way of the uncovered adhesive layer 620.

Next, a procedure for using the hemostatic device 600 according to the second embodiment will be described.

While the operator causes the sheath tube 210 of the introducer 200 to indwell the radial artery side Pdr of the palmar artery Pa (refer to FIG. 8), the operator disposes or positions the covering portion 610 to cover the site where bleeding is to be stopped t1 formed on the dorsal side Hb of the hand of the patient. In this case, the operator can secure the hemostatic device 600 to the hand H of the patient by affixing the adhesive layer 620 of the covering portion 610 to the dorsal side Hb of the hand H of the patient.

Next, the operator connects the syringe to the connector 173 of the injection portion 170, and injects air into the pressing portion 160. The pressing portion 160 is inflated by injecting the air into the pressing portion 160 so as to apply the compressing force to the puncture site t2 formed on the radial artery side Pdr of the palmar artery Pa (refer to FIG. 19).

While maintaining the compressing force of the pressing portion 160 which is applied to the puncture site t2, the operator removes the sheath tube 210 of the introducer 200 from the puncture site t2.

The patient can move the arm A, the wrist W, and the fingertip, while the hemostasis is performed using the hemostatic device 600. Therefore, the patient can more freely move his or her body, compared to a case of the hemostasis in a state where the compressing force is applied to the puncture site formed on the arm or the wrist. Accordingly, QOL is improved.

In addition, the hemostatic device 600 has a relatively simple structure in which the covering portion 610 is secured by the adhesive layer 620 in a state where the covering portion 610 covers the site where bleeding is to be stopped t1. The hemostatic device 600 does not have the restriction portion or the securing portion disposed between the adjacent fingers. Accordingly, work for wearing the hemostatic device 600 on the hand H of the patient is facilitated.

The operator removes the hemostatic device 600 from the dorsal side Hb of the hand of the patient after a predetermined time elapses and the hemostasis is completely performed on the puncture site t2. In this case, the operator can detach the hemostatic device 600 by carrying out simple work for separating the covering portion 610 from the dorsal side Hb of the hand of the patient.

As described above, according to the hemostatic method according to the second embodiment, in a state where the covering portion 610 covers the site of bleeding is to be stopped t1 of the hand H of the patient, the operator can cause the pressing portion 160 to apply the compressing force to the site where bleeding is to be stopped t1. Therefore, during the hemostasis, the patient can more freely move the arm A, the wrist W, and the fingers F1 to F5. Accordingly, QOL is improved.

Next, a modification example according to the above-described second embodiment will be described. Note that, in the modification example, configurations and materials which are not specifically described or medical procedures (procedures of the hemostatic method) which are not specifically described can be regarded as those according to the above-described second embodiment, and thus, description thereof will be omitted.

Modification Example

In a hemostatic device 700 according to a modification example, a configuration of the pressing portion is different from that of the hemostatic device 600 according to the above-described second embodiment.

Figure 20:
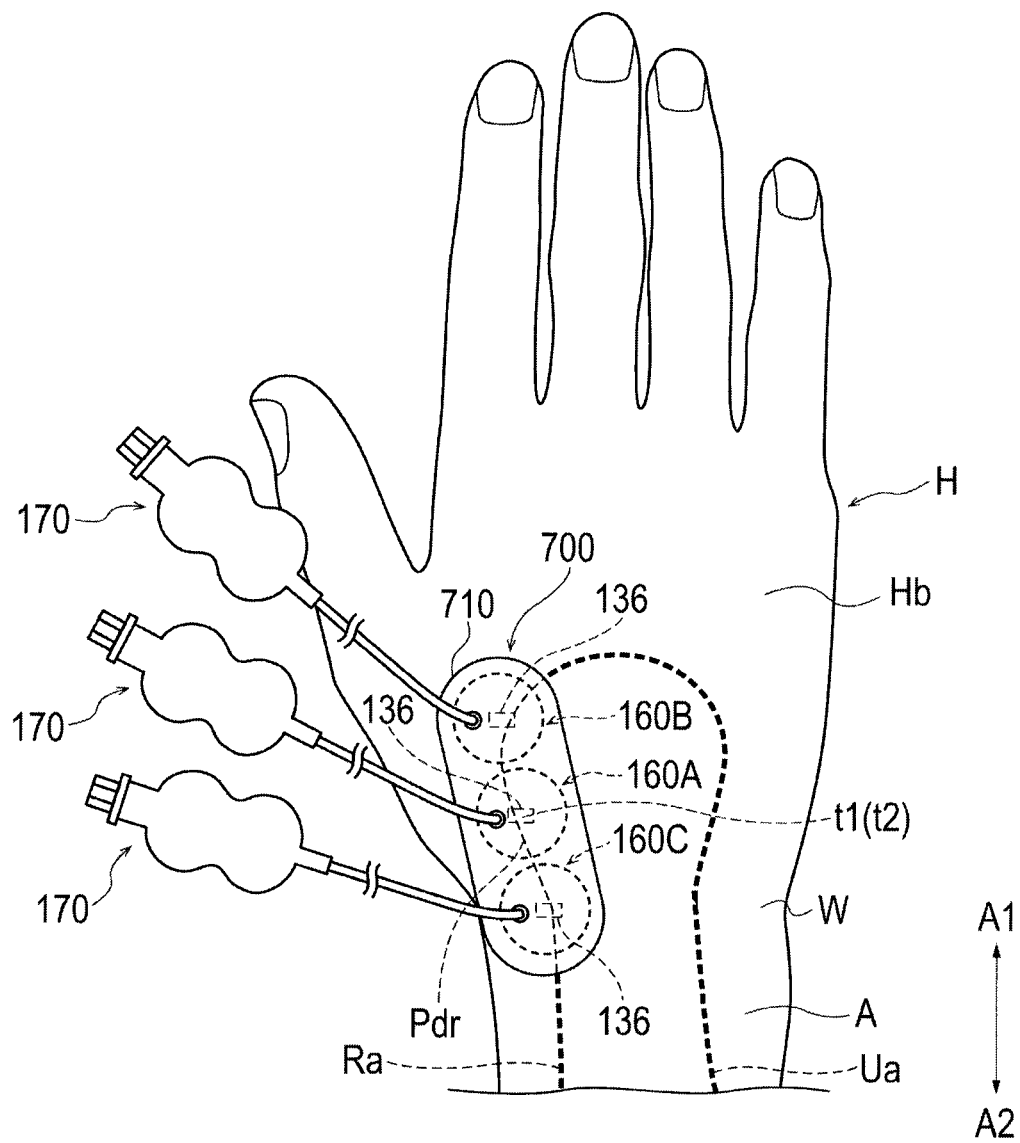
FIG. 20 is a plan view illustrating a state where a hemostatic device according to a modification example of the second embodiment is worn on the hand of the patient.

As illustrated in FIG. 20, the hemostatic device 700 has a covering portion 710 disposed so as to cover the site where bleeding is to be stopped t1 on the hand H of the patient, and a first pressing portion 160A which compresses the site where bleeding is to be stopped t1 in a state where the covering portion 710 covers the site where bleeding is to be stopped t1. Furthermore, the hemostatic device 700 has a first pressing portion 160A and a second pressing portion 160B adjacent thereto so as to extend along the running or extending direction of the radial artery side Pdr of the palmar artery Pa, and a third pressing portion 160C similarly adjacent to the first pressing portion 160A.

The second pressing portion 160B is disposed on the fingertip side from the first pressing portion 160A. The third pressing portion 160C is disposed on the arm A side from the first pressing portion 160A.

The respective pressing portions 160A, 160B, and 160C are configured to be independently inflatable and deflatable by the air injected from the respectively connected injection portions 170.

Similar to the hemostatic device 500 according to the above-described second embodiment, the respective pressing portions 160A, 160B and 160C are disposed on the inner surface of the covering portion 710. The specific configuration of the respective pressing portions 160A, 160B, and 160C is substantially the same as that of the pressing portion 160 of the hemostatic device 600 according to the second embodiment.

The inner surface of the covering portion 710 is provided with an adhesive layer for securing the covering portion 710 to the hand H of the patient.

Next, a procedure for using the hemostatic device 700 according to this modification example will be described.

While the sheath tube 210 of the introducer 200 is indwelled in the radial artery side Pdr of the patient's palmar artery Pa (refer to FIG. 8), the operator disposes the covering portion 610 so as to cover the site where bleeding is to be stopped t1 formed on the dorsal side Hb of the hand of the patient. In this case, the operator disposes the first pressing portion 160A so as to overlap the site where bleeding is to be stopped t1, and disposes the second pressing portion 1606 and the third pressing portion 160C so as to overlap the radial artery side Pdr of the palmar artery Pa.

The operator secures the hemostatic device 700 to the hand H of the patient by affixing the adhesive layer 620 of the covering portion 610 to the surface of the dorsal side Hb of the hand of the patient.

Next, the operator connects the syringe to the connector 173 of the injection portion 170 connected to the first pressing portion 160A, and injects the air into the first pressing portion 160A. The pressing portion 160 is inflated by injecting the air into the pressing portion 160 so as to apply the compressing force to the puncture site t2 formed on the radial artery side Pdr of the palmar artery Pa.

Next, the operator injects air into the respective pressing portions 160B and 160C via the injection portion 170 connected to the second pressing portion 160B and the injection portion 170 connected to the third pressing portion 160C. In this case, the compressing force (inflated amount) applied by the respective pressing portions 160B and 160C is suppressed to a certain degree of magnitude relative to the compressing force of the first pressing portion 160A. That is, the second pressing portion 160B and the third pressing portion 160C are inflated and apply a compression force reduced relative to the compressing force of the first pressing portion 160A to a portion disposed at the second pressing portion 160B and the third pressing portion 160C. The hemostatic device 700 causes the second pressing portion 160B and the third pressing portion 160C to apply the compressing force to the radial artery side Pdr of the palmar artery Pa. In this manner, the hemostatic device 700 reduces the pressure (flow pressure) of the blood flowing in the vicinity where the first pressing portion 160A is disposed.

The order of inflating the second pressing portion 160B and the order of the third pressing portion 160C are not the same as each other. For example, both of these may be inflated at the same time.

Next, the operator discharges the air from the first pressing portion 160A via the injection portion 170 connected to the first pressing portion 160A. Through this operation, the operator decreases the compressing force of the first pressing portion 160A to such an extent that blood does not flow out of the site where bleeding is to be stopped t1.

Next, the operator removes the sheath tube 210 of the introducer 200 from the puncture site t2.

The hemostatic device 700 causes the second pressing portion 160B and the third pressing portion 160C to apply the compressing force to the radial artery side Pdr of the palmar artery Pa, thereby reducing the pressure (flow pressure) of the blood flowing in the vicinity where the first pressing portion 160A is disposed. Accordingly, even in a state where the compressing force applied to the puncture site t2 by the first pressing portion 160A is suppressed, it is possible to prevent the blood from flowing out of the site where bleeding is to be stopped t1. In addition, the hemostatic device 700 can perform the hemostasis while maintaining a state where the puncture site t2 is open. Therefore, during the hemostasis, the radial artery side Pdr of the palmar artery Pa can be prevented from being occluded.

The number of the pressing portions disposed in the hemostatic device 700 is not particularly limited, as long as three or more (the first pressing portion 160A and the two pressing portions 160B and 160C disposed so as to interpose the first pressing portion 160A therebetween) are provided. In addition, in order that the hemostatic method described in this modification example can be realized, it is preferable that the respective pressing portions disposed in the hemostatic device 700 are configured to be respectively and independently inflatable.

The inventive hemostatic device and the hemostatic method disclosed here have been described with reference to a plurality of the embodiments and modification examples. However, the present invention is not limited to the respective configurations described above, and can be appropriately modified, while falling within the scope of the appended claims.

For example, an applicable target of the hemostatic device is not limited to the blood vessel as long as the blood vessel serving as the applicable target is the palmar artery running in the hand. Specifically, in the respective embodiments, (i) an example has been described in which hemostasis is performed on the puncture site formed on the radial artery side Pdr of the deep palmar artery Pd of the palmar artery Pa. However, the hemostatic device can be used for hemostasis such as, for example, (ii) hemostasis of the puncture site formed on the ulnar artery side Pdu of the deep palmar artery Pd of the palmar artery Pa, (iii) hemostasis of the puncture site formed on the radial artery side Pfr of the superficial palmar artery Pf of the palmar artery Pa, and (iv) hemostasis of the puncture site formed on the ulnar artery side Pfu of the superficial palmar artery Pf of the palmar artery Pa (refer to FIG. 6).

In a case where the hemostatic device is used for the hemostasis of (iii) and (iv) described above, it is preferable to adopt a configuration so that the pressing portion is disposed on the palm Hp side. The superficial palmar artery Pf of the palmar artery Pa runs at a position close to the palm Hp side rather than the side of the dorsal side Hb of the hand. Accordingly, the operator applies the compressing force from the palm Hp side. In this manner, hemostasis can be preferably performed. In this case, the puncture site can be formed through the puncturing from the palm side of the patient.

In addition, the hemostatic method is not particularly limited to a specific hemostasis position (position to which the compressing force is applied), as long as an object of the hemostasis is the puncture site formed on the radial artery side of the palmar artery in which the blood vessel serving as the applicable target runs in the hand. For example, the hemostatic method is not limited to the hemostasis of the puncture site formed on the radial artery side Pdr of the deep palmar artery Pd of the palmar artery Pa, and is also applicable to the hemostasis of the puncture site formed on the radial artery side Pfr of the superficial palmar artery Pf of the palmar artery Pa (refer to FIG. 6).

In addition, the hand on which the puncture site is formed may be either the right hand or the left hand of the patient.

In addition, in the respective embodiments, an example has been described in which the sheath tube of the introducer is used as the medical elongated body inserted into the palmar artery via the puncture site. However, a specific type of the medical elongated body is not particularly limited. For example, a guide wire or a guiding sheath may be used.

In addition, the hemostatic device described in the respective embodiments and modification examples is merely an example. Each portion configuring the hemostatic device can be replaced with any desired configuration capable of fulfilling the same function. In addition, the hemostatic device may be appropriately provided with any additional configuration element (member) which is not specifically described herein.

The detailed description above describes embodiments and modification examples of a hemostatic device and hemostatic method which collectively represent examples of the inventive hemostatic device and hemostatic method disclosed here. The invention is not limited, however, to the precise embodiments, modifications and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
   a covering portion configured to cover a site where bleeding is to be stopped on a hand of a patient;
   a pressing portion that compresses the site where bleeding is to be stopped when the covering portion covers the site where bleeding is to be stopped;
   a marker portion for aligning the pressing portion with the site where bleeding is to be stopped so that the pressing portion overlies the site where bleeding is to be stopped;
   the covering portion including:
   a securing portion configured to surround at least a portion of the patient's hand while covering the pressing portion, and
   a restriction portion that restricts movement of the securing portion in an axial direction;
   the restriction portion being positionable between adjacent fingers of the patient's hand;
   the securing portion including:
   a band portion wrappable around a periphery of the patient's hand at the site where bleeding is to be stopped, the band portion including a midpoint between oppositely located first and second free ends of the band portion, the pressing portion being mounted on the band portion at an intermediate position between the first and second free ends of the band portion, the pressing portion being located closer to the first free end of the band portion than the second free end of the band portion, the band portion including an elongated part that extends from the second free end of the band portion toward the pressing portion, the elongated part of the band portion possessing a centerline that extends along the elongated part of the band portion from the second free end to the midpoint of the band portion, the centerline of the elongated part of the band portion intersecting the second free end of the band portion at a first point; and
   a holding portion that secures the band portion in a state in which the band portion is wrapped around the periphery of the patient's hand at the site where bleeding is to stopped;
   the restriction portion including:
   a first end portion secured to the band portion;
   a second end portion that is a free end portion configured to be freely detachably interlocked with the band portion;
   a midpoint between the first end portion of the restriction portion and the second free end portion of the restriction portion;
   an elongated part that extends from the second free end portion of the restriction portion toward the band portion, the elongated part of the restriction portion possessing a centerline that extends along the elongated part of the restriction portion from the second free end portion to the midpoint of the restriction portion, the centerline of the elongated part of the restricted portion intersecting the second free end of the restriction portion at a second point;
   the centerline of the elongated part of the restriction portion, the centerline of the elongated part of the band portion and a straight line connecting the first and second points forming a triangle; and
   the centerline of the elongated part of the restriction portion and the centerline of the elongated part of the band portion forming an included angle of the triangle that is an obtuse angle.

2. The hemostatic device according to claim 1, wherein the restriction portion is configured so that when the second end portion of the restriction portion is detachably interlocked with the band portion, an intermediate portion of the restriction portion located between the first and second end portions of the restriction portion passes between a thumb of the patient's hand and a forefinger of the patient's hand, in a state in which the band portion is wrapped around the periphery of the patient's hand.

3. The hemostatic device according to claim 2, wherein the covering portion is configured and the pressing portion is positioned relative to the covering portion such that in a state in which the second end portion of the restriction portion is detachably interlocked with the band portion, the pressing portion is disposed on a root side of the patient's thumb from the second end portion of the restriction portion.

4. The hemostatic device according to claim 2, wherein the marker portion and the pressing portion are positioned in overlying relation to one another.

5. The hemostatic device according to claim 1, wherein the restriction portion includes a liquid absorbing layer that possesses a liquid absorbing property to absorb liquid when the restriction portion is positioned between the adjacent fingers, the liquid absorbing layer being positioned on a side of the restriction portion that faces the patient's hand when the restriction portion is positioned between the adjacent fingers.

6. The hemostatic device according to claim 1, wherein the covering portion includes a through opening that passes through the covering portion to enable a medical elongated body to pass through the through opening and indwell at the site where bleeding is to be stopped.

7. The hemostatic device according to claim 1, wherein the securing portion is a surrounding portion which is configured to surround a whole dorsal side of the patient's hand while being in contact with a surface of the dorsal side of the hand, and the restriction portion is formed integrally in one piece with the surrounding portion and passes between the adjacent fingers of the hand in a state in which the surrounding portion is wrapped around the dorsal side of the patient's hand.

8. The hemostatic device according to claim 7, wherein the surrounding portion includes a through opening that passes through the surrounding portion to enable a medical elongated body to pass through the through opening and indwell at the site where bleeding is to be stopped, and the through opening being disposed between a thumb of the patient's hand and a forefinger of the patient's hand in a state in which the surrounding portion is wrapped around the dorsal side of the patient's hand.

9. The hemostatic device according to claim 8, wherein the through opening is disposed on a side of the thumb from the pressing portion in the state in which the surrounding portion is wrapped around the dorsal side of the patient's hand.

10. The hemostatic device according to claim 1, wherein the band portion and the restriction portion each possess a width, the width of the band portion being greater than the width of the restriction portion.

11. A hemostatic device comprising:
a covering portion configured to cover a site where bleeding is to be stopped on a hand of a patient;
a pressing portion that compresses the site where bleeding is to be stopped when the covering portion covers the site where bleeding is to be stopped;
a marker portion for aligning the pressing portion with the site where bleeding is to be stopped so that the pressing portion overlies the site where bleeding is to be stopped;
the covering portion including:
a securing portion configured to surround at least a portion of the patient's hand while covering the pressing portion, and
a restriction portion that restricts movement of the securing portion in an axial direction;
the restriction portion being positionable between adjacent fingers of the patient's hand;
the securing portion including:
a band portion wrappable around a periphery of the patient's hand at the site where bleeding is to stopped, the band portion including a midpoint between oppositely located first and second free ends of the band portion, the pressing portion being mounted on the band portion at an intermediate position between the first and second free ends of the band portion, the pressing portion being located closer to the first free end of the band portion than the second free end of the band portion, the band portion including an elongated part that extends from the second free end of the band portion toward the pressing portion, the elongated part of the band portion possessing oppositely extending sides that extend along the elongated part of the band portion from the second free end to the midpoint of the band portion, at least a portion of one of the sides of the elongated part of the band portion being a straight side portion; and
a holding portion that secures the band portion in a state in which the band portion is wrapped around the periphery of the patient's hand at the site where bleeding is to stopped;
the restriction portion including:
a first end portion secured to the band portion;
a second end portion that is a free end portion configured to be freely detachably interlocked with the band portion;
a midpoint between the first end portion of the restriction portion and the second free end portion of the restriction portion; and
an elongated part that extends from the second free end portion of the restriction portion toward the band portion, the elongated part of the restriction portion possessing oppositely extending sides that extend along the elongated part of the restriction portion from the second free end portion of the restriction portion to the midpoint of the restriction portion, at least a portion of one of the sides of the elongated part of the restriction portion being a straight side portion,
the straight side portion of the elongated part of the restriction portion and the straight side portion of the elongated part of the band portion forming an angle that is an obtuse angle.

12. The hemostatic device according to claim 11, wherein the marker portion and the pressing portion are positioned in overlying relation to one another.

13. The hemostatic device according to claim 11, wherein the restriction portion includes a liquid absorbing layer that possesses a liquid absorbing property to absorb liquid when the restriction portion is positioned between the adjacent fingers, the liquid absorbing layer being positioned on a side of the restriction portion that faces the patient's hand when the restriction portion is positioned between the adjacent fingers.

14. The hemostatic device according to claim 11, wherein the covering portion includes a through opening that passes through the covering portion to enable a medical elongated body to pass through the through opening and indwell at the site where bleeding is to be stopped.

15. The hemostatic device according to claim 11, wherein the band portion and the restriction portion each possess a width, the width of the band portion being greater than the width of the restriction portion.

16. A hemostatic device comprising:
a covering portion configured to cover a site where bleeding is to be stopped on a hand of a patient;
a pressing portion that compresses the site where bleeding is to be stopped when the covering portion covers the site where bleeding is to be stopped;
a marker portion for aligning the pressing portion with the site where bleeding is to be stopped so that the pressing portion overlies the site where bleeding is to be stopped;
the covering portion including:
a securing portion configured to surround at least a portion of the patient's hand while covering the pressing portion, and a restriction portion that restricts movement of the securing portion in an axial direction;

the restriction portion being positionable between adjacent fingers of the patient's hand;

the securing portion including:

a band portion wrappable around a periphery of the patient's hand at the site where bleeding is to stopped, the band portion including a midpoint between oppositely located first and second free ends of the band portion, the pressing portion being mounted on the band portion at an intermediate position between the first and second free ends of the band portion, the pressing portion being located closer to the first free end of the band portion than the second free end of the band portion, the band portion including an elongated part that extends from the second free end of the band portion toward the pressing portion, the elongated part of the band portion possessing a centerline that extends along the elongated part of the band portion from the second free end to the midpoint of the band portion, the elongated part of the band portion possessing a width; and a holding portion that secures the band portion in a state in which the band portion is wrapped around the periphery of the patient's hand at the site where bleeding is to stopped;

the restriction portion including:

a first end portion secured to the band portion;

a second end portion that is a free end portion configured to be freely detachably interlocked with the band portion;

a midpoint between the first end portion of the restriction portion and the second free end portion of the restriction portion;

an elongated part that extends from the second free end portion of the restriction portion toward the band portion, the elongated part of the restriction portion possessing a centerline that extends along the elongated part of the restriction portion from the second free end portion to the midpoint of the restriction portion, the elongated part of the restriction portion possessing a width;

the width of the elongated part of the band portion along its entire extent being greater than the width of the elongated part of the restriction portion along its entire extent; and the centerline of the elongated part of the restriction portion and the centerline of the elongated part of the band portion forming an included angle that is an obtuse angle.

17. The hemostatic device according to claim 16, wherein the marker portion and the pressing portion are positioned in overlying relation to one another.

18. The hemostatic device according to claim 16, wherein the restriction portion includes a liquid absorbing layer that possesses a liquid absorbing property to absorb liquid when the restriction portion is positioned between the adjacent fingers, the liquid absorbing layer being positioned on a side of the restriction portion that faces the patient's hand when the restriction portion is positioned between the adjacent fingers.

19. The hemostatic device according to claim 16, wherein the covering portion includes a through opening that passes through the covering portion to enable a medical elongated body to pass through the through opening and indwell at the site where bleeding is to be stopped.

* * * * *